United States Patent [19]

Eugster et al.

[11] Patent Number: 5,270,041
[45] Date of Patent: Dec. 14, 1993

[54] STEROLS, THEIR FATTY ACID ESTERS AND GLUCOSIDES; PROCESSES FOR THEIR PREPARATION; SPONTANEOUSLY DISPERSIBLE AGENTS CONTAINING THESE COMPOUNDS, AND THEIR USE FOR TREATMENT OF TUMORS

[75] Inventors: Carl Eugster, Riehen; Conrad Eugster, Wallisellen; Walter Haldemann, Binningen, all of Switzerland; Giorgio Rivara, Turin, Italy

[73] Assignee: Marigen S.A., Riehen, Switzerland

[21] Appl. No.: 634,215

[22] PCT Filed: Jul. 6, 1990

[86] PCT No.: PCT/CH90/00164
  § 371 Date: Feb. 15, 1991
  § 102(e) Date: Feb. 15, 1991

[87] PCT Pub. No.: WO91/01139
  PCT Pub. Date: Feb. 7, 1991

[30] Foreign Application Priority Data

Jul. 21, 1989 [CH] Switzerland ............ 2727/89
Dec. 2, 1989 [CH] Switzerland ............ 4308/89

[51] Int. Cl.$^5$ .................... A61K 35/78; C07J 17/00
[52] U.S. Cl. ..................... 424/195.1; 536/5; 536/62; 552/540; 552/547; 552/544; 552/545; 549/408; 568/824
[58] Field of Search ........... 424/195.1; 552/540; 514/783; 536/5, 6.2; 532/502

[56] References Cited

U.S. PATENT DOCUMENTS

| 207,368 | 8/1878 | Powers | 424/195.1 |
|---|---|---|---|
| 1,626,321 | 4/1927 | Barksdale | 424/195.1 |
| 2,242,062 | 5/1941 | Evertz | 424/195.1 |
| 2,448,185 | 8/1948 | Levin | 424/195.1 |
| 3,219,542 | 11/1965 | Lammers | 424/195.1 |
| 3,495,011 | 2/1970 | L'Oreal | 424/312 |

FOREIGN PATENT DOCUMENTS

| 0289636 | 11/1988 | European Pat. Off. |
|---|---|---|
| 931115 | 7/1963 | United Kingdom . |
| 2043649 | 10/1980 | United Kingdom . |
| 2166107 | 4/1982 | United Kingdom . |

OTHER PUBLICATIONS

Steinmetz, E. F. Codex Vegetabilis 1957 Amsterdam #365, 543.
The Merck Index 9th ed. 1976 Merck & Co., Rahway, N.J. #5075.
Chemical Abstracts 99 5 38672c Zdzislaw (1983).
Chemical Abstracts 106 5 30226c Goad (1986).
Chemical Abstracts 113 9 74872j Akihisa (1990).
*Chemical Abstracts,* vol. 115, 1991 Abstract No. 287165j, Carl Eugster et al., Esters and glucosides of sterols from seeds..., PCT Int'l Appln. No. WO 9101,139, Feb. 7, 1991, Ch Appln. 89/2,727, Jul. 21, 1989, p. 63.
*Chemical Abstracts,* vol. 115, 1991 Abstract No. 287167m, Ikegami, Susumu; Isolation of steroidal saponins as antitumor agents; May 16, 1991, Appln. 89/252,646, Sep. 28, 1989, p. 5.
*Chemical Abstracts,* vol. 115, 1991 Abstract No. 287170g, Oka, Hiroshi et al., Manufacture of antitumor substance... Jpn. Koki Tokyo Koho Jp 03,197,481, Aug. 28, 1991, Appl. 89/338,930, Dec. 27, 1982, p. 11.

*Primary Examiner*—Michael G. Wityshyn
*Assistant Examiner*—Ralph Gitomer
*Attorney, Agent, or Firm*—Wegner, Cantor, Mueller & Player

[57] ABSTRACT

There are described antitumour sterols, their fatty acid esters and glucosides, processes for their preparation, spontaneously dispersible agents containing these sterols, their fatty acid esters and glucosides, and their use for treating tumours.

10 Claims, 6 Drawing Sheets

SCHMELZPUNKTE

Gemessen mit einem Mettler-Gerät TA 4000  DSC-Verfahren
(Differential Scanning Calorimetry)   Rate: 2.5°C/min.,
bzw. mit einem Büchi-Gerät No. 535

| MESSWERT VERBINDUNG | ONSET (Smp) | PEAK °C | ENDOTHERME REAKTION |
|---|---|---|---|
| C 8:0 CHOLESTEROL | 106,6 | 107,6 | 103 - 110 |
| C 8:0 SITOSTEROL | 71,3 | 72,5 | 64 - 76 |
| C 8:0 STIGMASTEROL | 89,9 | | 89,5 - 90,4 |
| C 11:1 CHOLESTEROL | 78,9 | 79,7 | 78 - 88 |
| C 11:1 SITOSTEROL | 68,3 | | |
| C 11:1 STIGMASTEROL | 85,7 | 86,7 | 80 - 90 |
| C 12:0 CHOLESTEROL | 79,4 | 79,9 | 76 - 82 |
| C 12:0 SITOSTEROL | 82,4 | 83,3 | 78 - 88 |
| C 12:0 STIGMASTEROL | 97,1 | 98,0 | 90 - 101 |
| C 16:0 CHOLESTEROL | 77 - 79 | | |
| C 16:0 SITOSTEROL | 89,6 | 91,0 | 82 - 95 |
| C 16:0 STIGMASTEROL | 99,7 | 101,3 | 92 - 105 |
| C 18:2 CHOLESTEROL | 62 | | |
| C 18:3 CHOLESTEROL | 35 - 36 | | |

STIGMASTEROL-8-d-GLUCOSID    255,9 - 256,7

BRECHUNGSINDEX

Gemessen mit einem Zeiss-Refraktometer

| VERBINDUNG | MESSWERT $n_D$ 20°C |
|---|---|
| C 12:1 CHOLESTEROL | 1,4807 |
| C 12:1 SITOSTEROL | 1,5118 |
| C 12:1 STIGMASTEROL | 1,4913 |
| C 18:1 SITOSTEROL | 1,4900 |
| C 18:1 STIGMASTEROL | 1,4900 |
| C 18:2 SITOSTEROL | 1,4866 |
| C 20:4 SITOSTEROL | 1,4950 |

Fig. 1

Density Scanning Calorimetry

R f - W E R T E

1%-Lösung in CH$_2$Cl$_2$, bandförmig aufgetragen 2 cm/2μl
LINOMAT III CAMAG   10 cm run
UV 366 nach 1:1 H$_2$SO$_4$/MeOH   2 min 120° C

| SYSTEM<br>VERBINDUNG | 1 | 2 | 3 | 4 | 5 | 6 | 7 |
|---|---|---|---|---|---|---|---|
| C 8:0 CHOL | 0,12 | 0,19 | 0,30 | 0,85 | 0.98 | 0,85 | 0,68 |
| C 11:1 CHOL | 0,25 | 0,30 | 0,43 | 0,80 | 0,96 | 0,83 | 0,72 |
| C 11:1 SITO | 0,24 | 0,25 | 0,35 | 0,89 | 0,91 | 0,81 | 0,67 |
| C 11:1 STIGMA | 0,23 | 0,24 | 0,35 | 0,88 | 0,90 | 0,80 | 0,65 |
| C 12:0 CHOL | 0,14 | 0,20 | 0,32 | 0,89 | 0,99 | 0,90 | 0,73 |
| C 12:0 SITO | 0,26 | 0,27 | 0,39 | 0,92 | 0,95 | 0,84 | 0,73 |
| C 12:0 STIGMA | 0,26 | 0,27 | 0,39 | 0,92 | 0,95 | 0,84 | 0,73 |
| C 12:1 CHOL | 0,56 | 0,60 | 0,58 | 0,98 | 0,95 | 0,96 | 0,95 |
| C 12:1 SITO | 0,56 | 0,60 | 0,58 | 0,98 | 0,95 | 0,96 | 0,95 |
| C 12:1 STIGMA | 0,56 | 0,60 | 0,58 | 0,98 | 0,95 | 0,96 | 0,95 |
| C 16:0 SITO | 0,28 | 0,29 | 0,41 | 0,93 | 0,97 | 0,87 | 0,77 |
| C 16:0 STIGMA | 0,28 | 0,29 | 0,41 | 0,93 | 0,97 | 0,86 | 0,78 |
| C 18:2 SITO | 0,65 | 0,65 | 0,64 | 0,95 | 0,98 | 0,97 | 0,94 |
| C 18:2 STIGMA | 0,65 | 0,65 | 0,64 | 0,95 | 0,98 | 0,98 | 0,94 |
| C 18:3 SITO | 0,65 | 0,65 | 0,64 | 0,94 | 0,97 | 0,97 | 0,94 |
| C 18:3 STIGMA | 0,65 | 0,65 | 0,64 | 0,94 | 0,98 | 0,98 | 0,93 |

Erklärung:

System 1   Platte Merck Art. 5715   Petrolether/Diethylether 98:2

System 2   do.   do.   97:3

System 3   do.   Cyclohexan/Ethylacetat   97:3

System 4   Platte Macherey Nagel RP 18 Art. 811'071
                       Petrolether/Diethylether 95:5

System 5   do.   n-Hexan/t.Butylmethylether/Aceton
                       90:5:5

System 6   do.   Petrolether/Cyclohexan/Ethylacetat/
                  H$_2$O                    48:48:3:1

System 7   do.   Petrolether/Diethylether   97:3

Fig. 3

STIGMASTEROL-β-d-GLUCOSID

Rf-WERTE

Auftrag 2 mg/1 ml = 0,2 % Lösung in $CHCl_3$ : MeOH : $H_2O$
                                                                                70 : 30 : 5
                       im Wasserbad auf 60 °C anwärmen System 1    Rf. 0,65
    System 2    Rf. 0,56
    System 3    Rf. 0,49
    System 4    Rf. 0,60

Erläuterung:
_____

System 1:    $CHCl_3$ : MeOH : 17%$NH_3$
                         41     41     18
    System 2:    $CHCl_3$ : MeOH : $H_2O$
                         70     30     5
    System 3:    $CHCl_3$ : MeOH : $H_2O$ : Essigsäure
                         75     25     5     0,5
    System 4:    n-Butanol : $CCl_4$ : MeOH : Ameisensäure : $H_2O$
                         30       40      20       5        5

DENSITY SCANNING CALORIMETRY

Mettler Gerät  TA 4000  Rate 2,5 °C/min.

STEROLS, THEIR FATTY ACID ESTERS AND GLUCOSIDES; PROCESSES FOR THEIR PREPARATION; SPONTANEOUSLY DISPERSIBLE AGENTS CONTAINING THESE COMPOUNDS, AND THEIR USE FOR TREATMENT OF TUMORS

INTRODUCTION

The present invention relates to sterols, their fatty acid esters and glucosides; to processes for their preparation; to spontaneously dispersible agents containing these compounds, and to their use for treatment of tumours.

Surprisingly, it has been found that mainly the sterols extracted from the seed of the sunflower (Helianthus annuus L.) and of certain pumpkin species (Cucurbita pepo L. and Cucurbita maxima Duch.), and the glucosides and in particular the fatty acid esters of these sterols, as well as the spontaneously dispersible agents prepared with these compounds, have an outstanding antitumoral action.

No mention is made in the literature that sterols, their glucosides and in particular their fatty acid esters, can be employed for the treatment of tumours.

BRIEF DESCRIPTION OF THE DRAWINGS

FIG. 1 shows the melting points and refractive indices of some exemplary sterols according to the present invention;

FIG. 3 provides the Rf values for some exemplary sterols according to the present invention;

FIG. 5 gives the Rf values for stigmasterol-beta-d-glucoside; and

DESCRIPTION OF THE INVENTION

Figure 2:
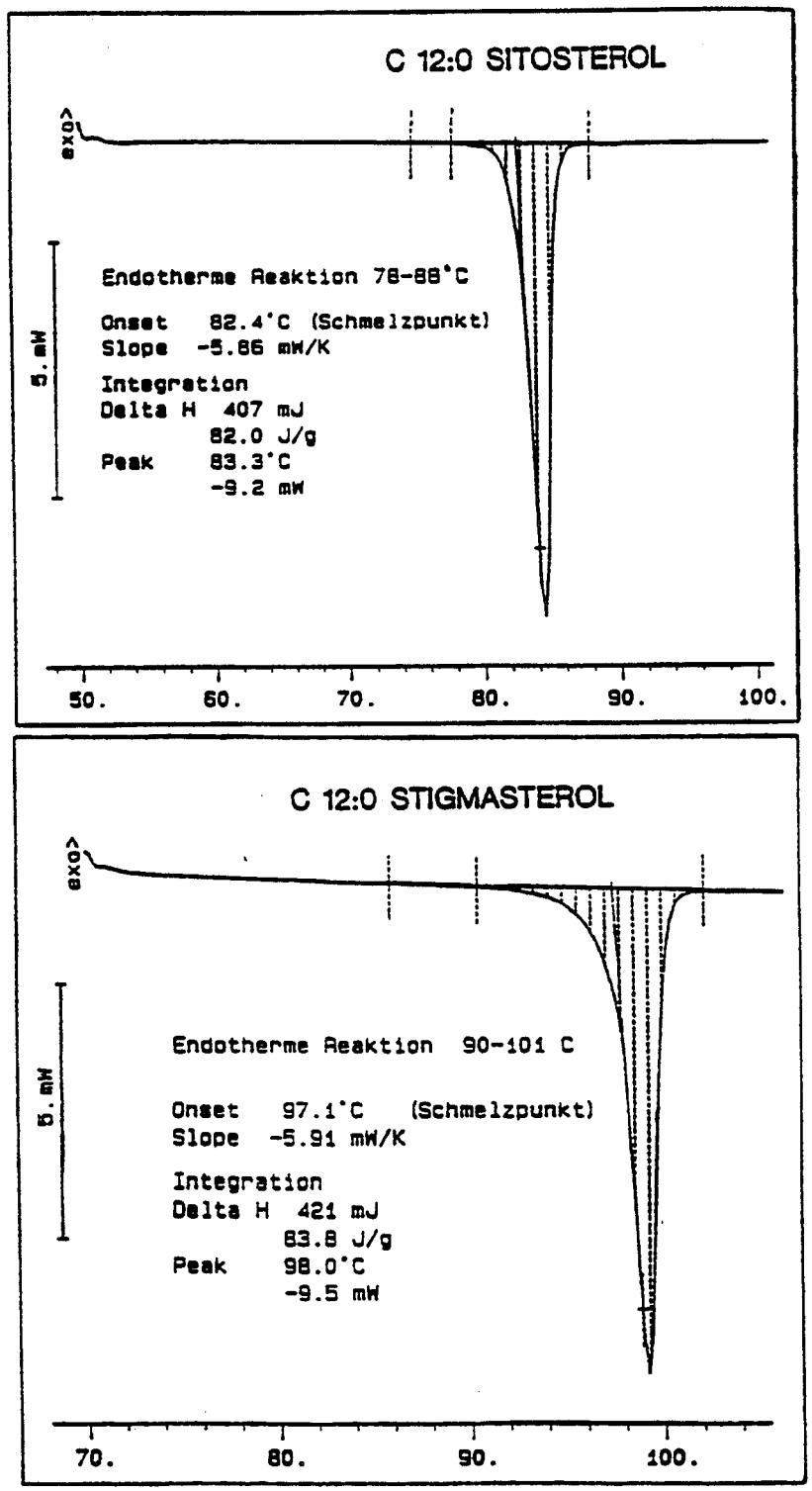
FIG. 2 shows the density scanning calorimetry graphs for sitosterol and stigmasterol.

Sterols, their fatty acid esters und glucosides to be used according to the invention can be obtained for example from preferably pregerminated seeds of Helianthus annuus L., Cucurbita pepo L. (varietas styriaca) or Cucurbita maxima Duch., by carrying out the following process steps:

The seeds which have been washed and pregerminated for 2 to 4 days are treated with distilled water which contains 0.1 to 3%, and preferably 0.1 to 1%, of mannitol and 0.1 to 4% of a pharmaceutically acceptable, non-ionic surfactant or surfactant mixture (relative to the pregerminated seeds). The mixture is homogenized in a toothed colloid mill, and the homogenate thus obtained is then centrifuged. The resulting three phases are separated from each other. The bottom phase which contains husk fragments and cell debris is discarded. The upper, oily phase is subjected to an extraction step and then purified by preparative chromatography, while the middle, aqueous phase is first subjected to ultrafiltration and then concentrated in vacuo and lyophilized as a concentrate. (See, in this context, Processing Examples 1 to 3).

The fatty acid esters of sterols, which are preferably to be used according to the invention, can generally also be prepared semisynthetically by the following processes which are known per se:

a) Reaction of the fatty acid with N,N'-carbonyldiimidazole at 25°–70° C. with the addition of a catalytic amount of an alcoholate in tetrahydrofuran, benzene, chloroform or dimethylformamide or in a similar indifferent solvent, followed by alcoholysis of the imidazolides formed with a sterol, such as, for example 24 β-Ethylcholesta - 5,22,25 - trien - 3β-ol (25,27 Dehydroporiferasterol)
24 β-Ethylcholesta - 5,25 (27) - dien - 3β-ol (Clerosterol)
24 z-Ethylidencholest - 5 - en - 3β-ol (Isofucosterol)
24 α-Ethylcholesta - 5,22 - dien -3β-ol (Δ5-Stigmasterol)
24 α-Ethylcholest - 5 - en - 3β-ol (Δ5-Sitosterol)
24 α-Ethylcholest - 7 - en - 3β-ol (Δ7-Sitosterol)
24 α-Ethyl - 5α - cholesta - 8,22 - dien - 3β-ol
24 β-Ethyl - 5α - cholesta - 8,25(27)-dien-3β-ol b) Formation of the chloride of the fatty acids with thionyl chloride in an indifferent solvent, followed by reaction of the fatty acid chloride formed with a sterol {in this context, see synthesis a)}.

The following straight-chain and branched, saturated and unsaturated fatty acids, inter alia, are suitable for syntheses a) and b):

valeric acid, isovaleric acid, sorbic acid, isocaproic acid, lauric acid, myristic acid, palmitic acid, stearic acid, arachidic acid, behenic acid, hexacosanoic acid, octacosanoic acid, pentadecanoic acid, heptadecanoic acid, nonadecanoic acid, tricosanoic acid, pentacosanoic acid, decenylic acid, undecenylic acid, dodecenylic acid, oleic acid, linoleic acid, linolenic acid, arachidonic acid, erucic acid, etc.

The glucosides of the sterols can be prepared by a process known per se, in such a manner that a steroid, such as, for example, sitosterol, stigmasterol or cholesterol, is reacted with acetobromoglucose in an inert solvent such as, for example, benzene, toluene, chloroform or tetrahydrofuran, in the presence of a catalyst such as, for example, silver carbonate.

Surprisingly, the spontaneously dispersible concentrates according to the invention possess an increased, in particular also a prophylactic, antitumour action. Treated with water, they give microemulsions having excellent phase stability and having improved permeability properties.

These spontaneously dispersible concentrates according to the invention contain

. 0.001 to 15% by weight of individual fatty acid esters of sterols, or combinations of these components, 0 to 40% by weight of a solvent or solvent mixture which is pharmaceutically acceptable and acts as a hydrotropic or co-emulsifier, 0.001 to 85% by weight of a pharmaceutically acceptable surfactant or surfactant mixture, 0 to 10% by weight of a vitamin or provitamin, 0 to 10% by weight of a free fatty acid, and, if appropriate, customary excipients and/or diluents.

The formulae of the fatty acid esters of sterols, to be used according to the invention, are as follows:

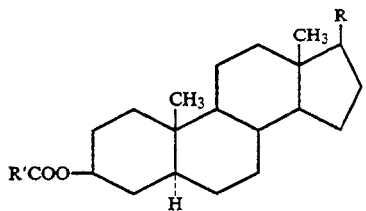 (I)

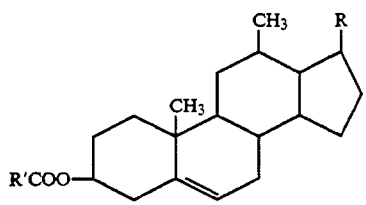 (II)

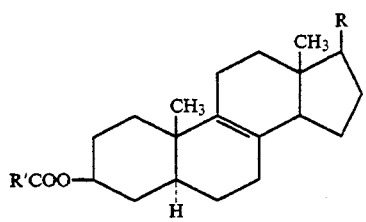 (III)

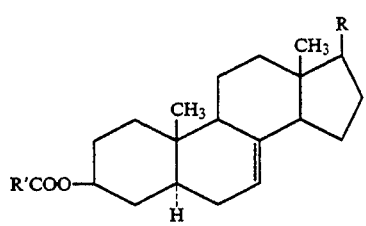 (IV)

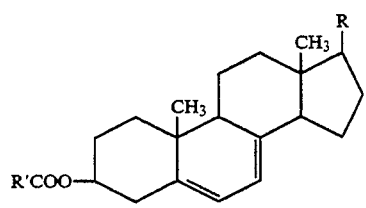 (V)

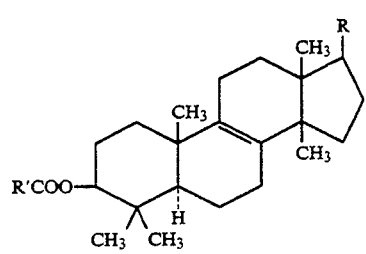 (VI)

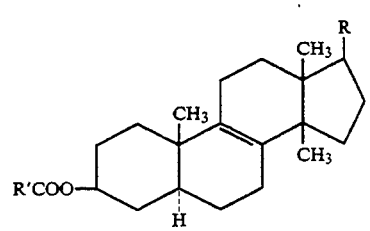 (VII)

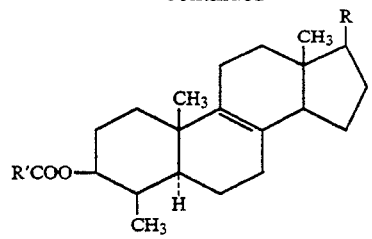 (VIII)

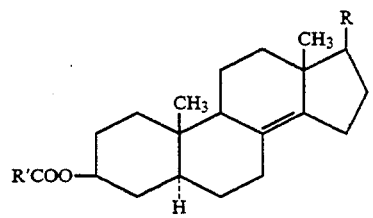 (IX)

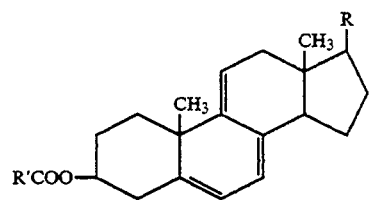 (X)

In formulae I-X, R denotes a $C_1$- to $C_{10}$-alkyl group or a $C_2$- to $C_{10}$-alkenyl group, and R' denotes a $C_1$- to $C_{32}$-alkyl group or a $C_2$- to $C_{32}$-alkenyl group or alkapolyene group (i.e. the corresponding alkadienes, alkatrienes, alkatetraenes, alkapentaenes or alkahexanenes). These side chains of R and R' can be straight-chain or branched.

In the case of R, the alkyl groups and the alkenyl groups have preferably 8-10 carbon atoms. Examples of such compounds are, inter alia:

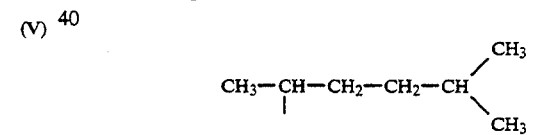

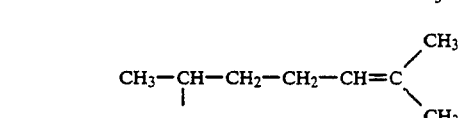

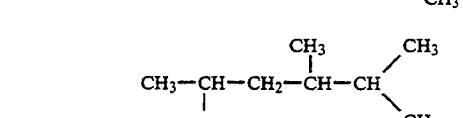

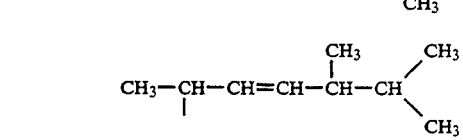

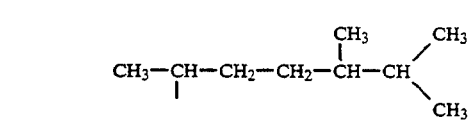

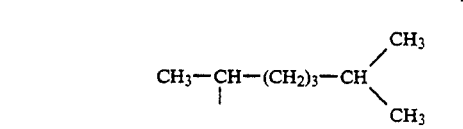

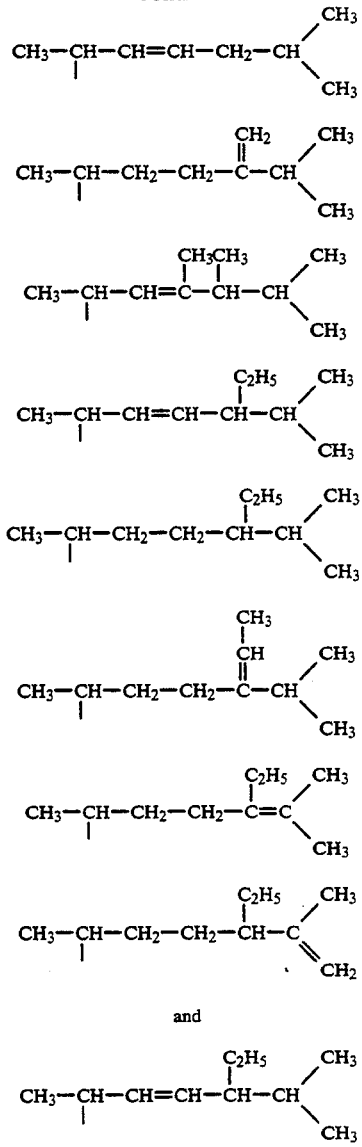

and

In the case of R', the alkyl and alkenyl/alkapolyene groups (having 1 to 6 double bonds) preferably have 8 to 22 carbon atoms. In the case of R', particularly preferred alkyl and alkenyl/alkapolyene groups are those having 10 to 18 carbon atoms.

Examples of fatty acid esters of sterols of the formulae I to X to be used according to the invention are, inter alia:

ergosta-5,7-dien-3-ol-9-hexadecenoate
(ergosta-5,7-dienylpalmitoleate)

ergosta-8,22-dien-3-ol-14-methyl-4,9-octadecenoate
(14α-methylergosta-8,22-dienyloleate)

lanost-8-en-3-ol-9-octadecenoate
(dihydrolanosterol-oleate)

ergost-5-en-3-ol-9,12,15-octadecatrienoate
(dihydrobrassicasteryl-linolenate)

ergost-5-en-3-ol-9,12-octadecadienoate
ergost-5-en-3-ol-9-octadecenoate
(dihydrobrassicasteryl-oleate)

ergosta-7,24 (28)-dien-3-ol-4-methyl-9-octadecenoate
(gramisteryl-oleate)

stigmasta-8,24 (28)-dien-3-ol-9,12-octadecadienoate
($\Delta^7$-avenasteryl-linoleate)

ergosta-7,24 (28)-dien-3-ol-4-methyl-9,12-octadecadienoate
(gramisteryl-linoleate)

stigmast-24 (28)-en-3-ol-9,12-octadecadienoate
ergosta-5,22-dien-3-ol-4,23-dimethyl-9-octadecenoate
ergostan-3-ol-4-methyl-9-octadecenoate
5α-stigmastan-3β-ol-linolenate
5α-stigmastan-3β-ol-oleate stigmastan-3-ol-9,12-octadecadienoate
(5α-stigmastan-3β-ol-linoleate)

22-dihydrospinasteryl-linoleate
ergosta-5,7,22-trien-3-ol-9,12-octa-decadienoate
(ergosterol-linoleate)

stigmasta-5,24 (28)-dien-3-ol-9-octadecenoate
stigmasta-5,24 (28)-3-ol-9,12-octadecadienoate
stigmasta-5-en-3-ol-5,8,11,14-eicosatetraenoate
(β-sitosterol-arachidonate)

ergost-5-en-3-ol-5,8,11,14-eicosatetraenoate
stigmasta-7,24 (28)-dien-3-ol-4-methyl-9,12-octadecadienoate
cholest-5-en-3-ol(3β)-9-hexadecenoate
(cholesteryl-trans-9-hexadecenoate)

ergost-7-en-3-ol-9,12,15-octadecatrienoate
ergost-5-en-3-ol-9,12,15-octadecatrienoate
(campesteryl-linolenate)

ergostan-3-ol-9,12-octadecadienoate
cholest-7-en-3-ol-9,12-octadecadienoate
ergosta 5,24 (28)-dien-3-ol-9-hexadecenoate
cholestan-3-ol-9-hexadecenoate ergosta-5,22-dien-3-ol-octadecenoate
(brassicasteryl-oleate)

cholest-7-en-3-ol-9-octadecenoate
(lathosteryl-oleate)

lanosta-8,24-dien-3-ol-9-octadecenoate
(lanosterol-oleate)

stigmasta-5,24(28)-dien-3-ol-9-octadecenoate
(fucosteryl-oleate)

cholesta-5,22-dien-3-ol-9-octadecenoate
(desmosteryl-oleate)

ergost-5-en-3-ol-12-octadecadienoate
(campesteryl-linoleate)

ergosta-5,22-dien-3-ol-9-octadecenoate
ergost-22-en-3-ol-9-hexadecenoate
ergosta-5,22-dien-3-ol-9-hexadecenoate
cholesta-5,22-dien-3-ol-9-hexadecenoate ergosta-5,22-dien-3-ol-9,12-octadecadienoate
brassicasteryl-linoleate)

ergosta-7,24(28)-dien-3-ol-9,12-octadecadienoate
stigmasta-5,22-dien-3-ol-9,12,15-octadecatrienoate
(stigmasterol-linolenate)

stigmasta-5,22-dien-3-ol-9,12-octadecadienoate
(stigmasterol-linoleate)

cholest-5-en-3-ol- (3β)-5,8,11,14-eicosatetraenoate
cholest-5-en-3-ol- (3β)-4,7,10,13,16,19-docosahexaenoate
cholest-5-en-3-ol- (3β)-9,12-octadecadienoate
cholesta-8,(14),24-dien-3-ol-9-octadecenoate
(zymosteryl-oleate)

ergost-5-en-3-ol-9-octadecenoate
(campesteryl-oleate)

cholesta-5,7,9 (11)-trien-3-ol-9-octadecenoate
(cholesta-5,7,9 (11)-trien-3β-yl-oleate)

ergosta-5,7,22-trien-3-ol-9-hexadecenoate
(ergosterol-9-hexadecenoate)

cholest-5-en-3-ol- (3β)-11-octadecenoate
(cholesterol-11-octadecenoate)

cholest-5-en-3-ol- (3β) 9,12-octadecadienoate
(cholesterol-9,12-octadecadienoate)

cholest-5-en-3-ol- (3β)-9-octadecenoate
(cholesterol-elaidate)

5α-stigmasta-7,22-dien-3β-ol-oleate
(α-spinasterol-oleate)

cholest-5-en-3-ol- (3β)-9-hexadecenoate
(cholesterol-palmitoleate)

cholestan-3-ol-9,12,15-octadecatrienoate
(cholestanol-linoleate)

cholest-5-en-3-ol- (3β)-11-octadecenoate
(cholesterol-11-octadecenoate)

cholesta-5,7-dien-3-ol-9-octadecenoate
cholesta-5,7-dien- (3β)-ol-linoleate
(cholecalciferol-linoleate)

ergosta-5,7,22-trien-3-ol-9-octadecenoate
(ergosterol-oleate)

stigmast-5-en-3-ol-9-octadecenoate
(β-sitosterol-oleate)

stigmast-5-en-3-ol-9,12-octadecadienoate
(β-sitosterol-linoleate)

stigmast-5-en-3-ol-9,12,15-octadecatrienoate
(β-sitosterol-linolenate)

cholest-5-en-3-ol- (3β)-9,12,15-octadecatrienoate
(cholesterol-linoleate)

cholestan-3-ol-9-octadecenoate
(cholestanol-oleate)

cholestan-3-ol-9,12-octadecadienoate
(cholestanol-linoleate)

cholest-5-en-3-ol- (3β)-9-hexadecenoate
(cholesterol-9-hexadecenoate)

cholest-5-en-3-ol- (3β)-5,8,11,14-eicosatetraenoate
(cholesterol-arachidonate)

cholest-5-en-3-ol- (3β)-9,12-octadecadienoate
(cholesterol-linoleat)e cholest-5-en-3-ol- (3β)-9-octaiecenoate
(cholesterol-oleat)e β-sitosterol-undecenoate
β-sitosterol-lauroylate
β-sitosterol-palmitate stigmasterol-undecenoate
stigmasterol-lauroylate
stigmasterol-palmitate The following examples of fatty acid esters of sterols, to be used according to the invention, are novel and likewise form part of the present invention:

γ-sitostanol-oleate
γ-sitostanol-linoleate
γ-sitostanol-linolenate
γ-sitosterol-oleate
cholest-5-en-3α-ol-oleate 5-α-stigmastan-3β-ol-oleate
5-α-stigmastan-3β-ol-linolenate
cholesta-5,7-dien-3β-ol-linoleate cholecalciferol-linolenate
10-α-ergosta-5,7,22-trien-3β-ol-linoleate
stigmast-5-en 3-ol-dodecenoate
(β-sitosterol-dodecenoate)

ergost-5-en-3-ol-dodecenoate
(campesteryl-dodecenoate)

cholest-7-en-3-ol-doiecenoate
stigmasta-5,22-dien-3-ol-doiecenoate
(stigmasterol-dodecenoate)

γ-sitosterol-dodecenoate
cholest-5-en-3-ol-undecenoate
cholest-5-en-3-ol-dodecenoate
5-cholesten-3-βol-dodecenoate The surfactants or surfactant mixtures to be employed according to the invention can be anionic, cationic, aphoteric or non-ionic. Ideally, they are non-ionic and have a HLB-value (i.e. a hydrophilic-lipophilic balance) of between 2 and 18; preferably, it is between 2 and 6 on the one hand and 10 and 15 on the other hand. HLB values describe the lipophilic and hydrophilic properties of an emulsifier. In this context see "Hydrophile-Lipophile Balance: History and recent Developments" by Paul Becher in Journal of Dispersion Science and Technology, 5 (1), 81–96 (1984).

Suitable anionic surfactants can be both so-called water-soluble soaps and water-soluble synthetic compounds.

Suitable soaps are the alkali metal salts, alkaline earth metal salts or optionally substituted ammonium salts of higher fatty acids ($C_{12}$ to $C_{22}$), for example the natural Na or K salts of oleic or stearic acids, or of natural mixtures of fatty acids which can be obtained, inter alia, from coconut oil or tallow oil. Other surfactants which may be mentioned are fatty acid methyltaurine salts, and modified and non-modified phospholipids.

However, more frequently used surfactants are so-called synthetic surfactants, in particular fatty sulfonates, fatty sulfates, sulfonated benzimidazole derivatives or alkylarylsulfonates.

The fatty sulfonates and fatty sulfates are usually present in the form of alkali metal salts, alkaline earth metal salts or optionally substituted ammonium salts and generally have an alkyl radical containing 8 to 22 C atoms, alkyl also encompassing the alkyl moiety of acyl radicals. Examples are the Na or Ca salt of ligninsulfonic acid, of dodecylsulfuric ester and sulfonic acids of fatty alcohol/ethylene oxide adducts. The sulfonated benzimidazole derivatives preferably contain two sulfonyl groups and one fatty acid radical containing about 8 to 22 C atoms. Alkylarylsulfonates are, for example, the Na, Ca or triethanolamine salts of dodecylbenzenesulfonic acid, of dibutylnaphthalenesulfonic acid or of a naphthalenesulfonic acid/formaldehyde condensation product. Other suitable compounds are the corresponding phosphates, such as, for example, salts of the phosphoric ester of a p-nonylphenol/(4–14)ethylene oxide adduct, or of an adduct of the formula

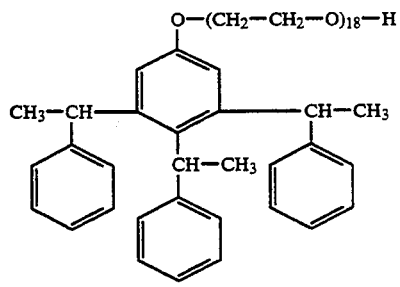

The non-ionic surfactants are mainly chosen from amongst the polyglycol ether derivatives of aliphatic or cycloaliphatic alcohols, saturated or unsaturated fatty acids and alkylphenols which can contain 3 to 30 glycol ether groups and 8 to 20 C atoms in the (aliphatic) hydrocarbon radical and 6 to 18 C atoms in the alkyl radical. Other suitable non-ionic surfactants are the water-soluble polyethyleneoxy adducts onto polypropylene glycol and alkyl polypropylene glycol with 1 to 10 C atoms in the alkyl chain, which adducts contain 20 to 250 ethylene glycol ether groups and 10 to 100 propylene ether groups. The compounds which have been mentioned customarily contain 1 to 5 ethylene units per propylene glycol unit.

The following may be mentioned as examples of non-ionic surfactants: nonylphenol polyethoxyethanols, castor oil polyglycol ethers, polypropylene/polyethylene oxide adducts, tributylphenoxy-polyethoxyethanol, polyethylene glycol and octylphenoxy-polyethoxyethanol. Moreover, fatty acid esters of polyoxyethylene sorbitan, such as polyoxyethylene sorbitan trioleate, are also suitable.

The cationic surfactants are mainly quaternary ammonium salts which contain at least one alkyl radical having 8 to 22 C atoms as the N-substituent and which have lower, optionally halogenated alkyl radicals, benzyl radicals or lower hydroxyalkyl radicals as further substituents. The salts are mainly present in the form of halides, methylsulfates or ethylsulfates, for example stearyltrimethylammonium chloride or benzyldi(2-chloroethyl)-ethylammonium bromide.

The following compounds may be employed as the pharmaceutically acceptable solvent which acts as the hydrotropic, or co-emulsifier, for example: esters of an aliphatic alcohol ($C_3$–$C_{18}$) with an aliphatic carboxylic acid ($C_{10}$–$C_{22}$), such as isopropyl laurate, hexyl laurate, decyl laurate, isopropyl myristate and lauryl myristate; hydrocarbons having a straight carbon chain ($C_{12}$–$C_{32}$) which is substituted by 6–16 methyl groups and which can have up to 6 double bonds, examples which may be mentioned being terpenes, such as polymethylbutanes and polymethylbutenes.

Monoesters of ethylene glycol or propylene glycol with an aliphatic carboxylic acid ($C_6$–$C_{22}$), such as propylene glycol monolaurate and propylene glycol monomyristate. Esters of an aliphatic alcohol ($C_{12}$–$C_{22}$) with lactic acid, such as, for example, myristyl lactate or, preferably, lauryl lactate. Monoesters or diesters of glycerol with an aliphatic carboxylic acid ($C_6$–$C_{22}$), such as, for example, glyceryl caprylate.

Esters of a poly(2–7)ethylene glycol glycerol ether having at least one free hydroxyl group with an aliphatic carboxylic acid ($C_6$–$C_{22}$), such as, for example, aliphatic alcohols ($C_{12}$–$C_{22}$), thus, inter alia, dodecanol, tetradodecanol, oleyl alcohol, 2-hexyldecanol and 2-octyldecanol.

Esters containing at least one free hydroxyl group, of poly (2–10)glycol with an aliphatic carboxylic acid ($C_6$–$C_{22}$), monoethers of a polyethylene glycol with an aliphatic alcohol ($C_{12}$–$C_{18}$), such as, for example, polyoxyethylene-($C_{10}$) octyl ether.

Suitable additives for the spontaneously dispersible concentrates according to the invention are vitamins and provitamins (such as, for example, vitamin A, retinoic acid, retinol, carotenes, tocopherols), and also free fatty acids, such as: valeric acid, isovaleric acid, sorbic acid, isocaproic acid, lauric acid, myristic acid, palmitic acid, stearic acid, arachidic acid, behenic acid, hexacosanoic acid, octacosanoic acid, pentadecanoic acid, decenylic acid, undecenylic acid, dodecenylic acid, oleic acid, linoleic acid, linolenic acid, arachidonic acid, erucic acid, etc.

The daily dose required for pharmaceutical administration is 0.001 to 25 mg/kg of body weight, if possible split into 2–3 individual doses. For this purpose, the fatty acid esters of sterols, or the spontaneously dispersible concentrates with these esters, can be incorporated into the conventional pharmaceutical preparations and dosage forms, such as coated tablets, tablets, capsules, powders, granules, pellets, solutions, ampuls, emulsions, creams or suppositories together with the customary excipients and/or diluents and stabilizers.

The active substances or mixtures of active substances which form the subject-matter of the invention, and the spontaneously dispersible concentrates which contain these active substances or mixtures of active substances, can be administered to humans orally, by injection (intravenously, subcutaneously or intramuscularly) or in other ways. If they are presented as solid dosage forms for oral administration, this can be in the form of tablets, granules, pellets, powders or capsules, etc. The preparations can contain additives, for example a pharmaceutical excipient, such as a saccharide or cellulose base, a binder, such as starch paste or methylcellulose, a filler, or a disintegrant, etc., with additives being employed which are customarily used in the preparation of medicinal or pharmaceutical formulations. When the active substances or mixtures of active substances according to the invention are administered orally in the form of liquid dosage forms, they can be present in any form selected from amongst aqueous preparations for internal use, from suspensions, emulsions and syrups, etc., and they can also be present in the form of dried preparations which are dissolved or emulsified prior to use.

When the active substances or mixtures of active substances according to the invention are processed in the form of aqueous solutions, suspensions or oily or aqueous emulsions, preferably microemulsions, from the spontaneously dispersible concentrates according to the invention, they can also be injected. However, it is customary to prepare the injection solutions shortly before administration, by dissolving or suspending the extracts or concentrates in aqueous, liquid media, such as sterile water or physiological sodium chloride solution or glucose solution.

If required, conventionally used solvents, stabilizers, preservatives and additives for the preparation of isotonic solutions can be added to a preparation for injection. The preparations for injection obtained in this manner are administered intravenously, intramuscularly, subcutaneously or in any other suitable way.

The present invention also relates to pharmaceutical preparations which contain the active substances, or mixtures of active substances, or the spontaneously dispersible concentrates which have been described, for controlling the growth of tumour cells. The pharmaceutical preparations according to the invention are those which can be used for enteral (such as oral or rectal) or for parenteral or topical administration to warm-blooded animals, which preparations contain the spontaneously dispersible concentrate on its own or together with a pharmaceutically acceptable excipient.

The dosage of the concentrates according to the invention depends on the warm-blooded species, on the age and on the individual condition, and on the mode of administration. For example, doses in the range of about 0.1–50 mg/kg of body weight are administered subcutaneously, and doses in the range of 0.05–5 mg/kg of body weight are administered intraperitoneally to warm-blooded animals having a low body weight, such as, for example, mice, rats and hamsters, to achieve an effect of tumour cell destruction.

The oral and rectal forms of the novel pharmacaeutical preparations contain between 1 and 95%, preferably between 10 and 95%, and in particular between 20 and 95%, of the spontaneously dispersible concentrate according to the invention. For example, they can be present in unit-type dosage forms, i.e., as coated tablets, micropellets, tablets, suppositories or ampuls and, in particular, as capsules.

Suitable pharmaceutically acceptable excipients for the oral forms are mainly fillers, such as sugars (for example lactose, sucrose, mannitol or sorbitol), cellulose preparations and/or calcium phosphates (for example tricalcium phosphate or calcium hydrogen phosphate), furthermore binders, such as starch paste, with the use of, inter alia, corn starch, wheat starch, rice starch or potato starch, gelatin, tragacanth, methylcellulose, hydroxymethylcellulose, sodium carboxymethylcellulose and/or polyvinylpyrrolidone and/or disintegrants (if desired), such as the above mentioned starches, furthermore carboxymethyl starch, cross-linked polyvinyl-pyrrolidone, agar, alginic acid or a salt thereof, for example sodium alginate.

Example of suitable flow-control agents are the polyethylene glycols Nos. 200–600 and above.

The gelatin capsules, which are the preferred dosage form for humans, are provided with suitable coatings, concentrated sugar solutions - which can optionally contain gum arabic, talc, polyvinylpyrrolidone, polyethylene glycol and/or titanium dioxide -, lacquer solutions (aqueous or those which have been prepared using organic solvents), or enteric coatings of solutions of suitable cellulose preparations, such as microcrystalline cellulose (Avicel), acetylcellulose phthalate, hydroxymethylcellulose phthalate, or a copolymer, such as Eudragit. L 30 D, being used, inter alia.

Pharmaceutical dosage forms for oral use which are particularly suitable according to the invention are two-piece gelatin capsules with a plasticizer, such as glycerol or sorbitol. The soft-gelatin or hard-gelatin capsule can contain the spontaneously dispersbile concentrate according to the invention as a mixture with fillers, such as lactose, binders, such as starch, and/or glidants, such as talc or magnesium stearate, and, if appropriate, together with stabilizers and antioxidants, such as, for example, α-tocopherol. It may be expedient to employ suitable liquids, such as liquid polyethylene glycols Nos. 200–600 as diluents, to which stabilizers and antioxidants can also be added.

For parenteral administration, distilled water is added to the concentrates according to the invention. To the aqueous microemulsion for injection which then forms, there can be added viscosity-increasing substances, for example Na-carboxymethylcellulose, sorbitol, mannitol and/or dextran, and if appropriate also stabilizers and antioxidants.

The pharmaceutical preparations for parenteral administration preferably contain between 0.1 and 60%, especially between 1 and 40%, of the spontaneously dispersible concentrate according to the invention.

Suitable preparations for topical use, which are particularly suitable for the prophylaxis of cancers of the skin, are, for example, creams, ointments, pastes, foams, tinctures and solutions, which contain between 0.001 and 70% of the concentrate according to the invention.

Oily bases which are used for creams and oil-in-water emulsions which contain more than 50% water, are mainly fatty alcohols, for example lauryl alcohol, cetyl alcohol or stearyl alcohol, waxes of liquid to solid consistency, for example isopropyl myristate, wool wax or beeswax and/or hydrocarbons, such as, for example, petroleum jelly (petrolatum) or paraffin oil. Substances which are mainly suitable for emulsifying these oily bases are surface-active, pharmaceutically acceptable substances having predominantly hydrophilic properties, such as, for example, non-ionic emulsifiers, in particular fatty acid esters of polyalcohols or ethylene oxide adducts (such as polyglycerol fatty acid esters or poleethylene sorbitan fatty acid esters) having an HLB value of less than 8. Additives which are added to the water phase are, inter alia, agents which prevent desiccation of the creams, for example polyalcohols, such as glycerol, sorbitol, propylene glycol and/or polyethylene glycols Nos. 200–600, and furthermore preservatives, odor-imparting substances, etc.

Ointments are water-in-oil emulsions which contain up to 70%, but preferably between 20 and 50%, water or aqueous phases.

Substances which are suitable as the lipid phase are mainly hydrocarbons, for example petroleum jelly, paraffin oil and/or solid paraffins, which contain hydroxy compounds suitable for improving the water-binding capacity, for example fatty alcohols or esters, such as cetyl alcohol or wool wax alcohols.

In some cases, emulsifiers having an HLB value of 8 to 16, such as, for example, sorbitan fatty acid esters (such as sorbitan isostearol) are also added. Additives which are added to the water phase are, inter alia, humectants, such as polyalcohols (glycerol, propylene glycol, sorbitol and/or polyethylene glycols No. 200, 400, 600); and furthermore preservatives, odor-imparting substances, etc.

Fatty ointments are anhydrous and chiefly contain hydrocarbons as the base, for example paraffin, petroleum jelly and/or liquid paraffins; moreover natural or partially-synthetic fats, such as, for example, coconut fatty acid triglyceride, furthermore: fatty acid partial esters of glycerol, such as, for example, the fatty alcohols, emulsifiers and/or additives which increase the water-absorption capacity, all of which have been mentioned in connection with the ointments.

Pastes are creams and ointments containing powder constituents which absorb secretions, such as, for example, metal oxides (such as titanium oxide or zinc oxide), and furthermore talc and/or aluminum silicates whose task it is to bind any moisture or discharge which may be present.

Foams are administered from pressurized containers and are oil-in-water emulsions of the spontaneously dispersible concentrates according to the invention which are present in aerosol form, with halogenated hydrocarbons (such as, for example, lower chlorofluoroalkanes; such as dichlorodifluoromethane and dichlorotetrafluorethane) being added as propellants. Other substances which may be added are the customary additives, such as preservatives, etc.

The present invention also relates to the use of the active substances, mixtures of active substances and spontaneuosly emulsifiable concentrates according to the invention for inhibiting the growth of tumour cells or as prophylactic agents against oncoses in humans and animals, administration preferably being carried out in the dosage forms which correspond to the pharmaceutical preparations described above. For use as dietary foods and as food additives, the optimum compositions must be established for every individual case.

PROCESSING EXAMPLES

1. Obtaining the lipophilic constituents and the aqueous extract 750 g of the husked seeds of Helianthus annuus L. (sunflower kernels) are moistened with distilled water and stored at 30° C. and 90% relative atmospheric humidity for 48 hours. The swelled pregerminated seeds, which now weigh 1,500 g, are treated with 1,500 ml of distilled water, 20 g of mannitol and 15 g of Invadin ® JFC 800% (a water-free non-ionic surfactant) (CIBA-GEIGY AG), and the mixture is homogenized using a Waring blender and a toothed colloid mill from Fryma AG, Rheinfelden. These 3 kg of homogenate are centrifuged for one hour at +4° C. and 10'000 rpm=18'100 g in a Suprafuge 22 (Heräus AG, Zurich). Three phases are formed. The upper lipophilic phase is removed, and the aqueous middle phase is separated from the bottom phase which contains the heavier fats and waxes as well as the cell debris.

2. Processing and analysis of the lipophilic constituents 200 g of the lipophilic phase from Processing Example 1 are dissolved in 400 ml of t-butyl methyl ether; the solution is freed of turbidity by filtration through filter paper. The solvent is then evaporated from the filtrate on a Rotavapor (Büchi Laboratoriums-Technik AG, Flawil) under a vacuum of 5 mm/Hg (diaphragm pump) and at a temperature gradient of from 35° C. to 3.5° C. The oil which remains is purified further by preparative chromatography.

Analysis of the purified oil of Helianthus annuus L. according to Processing Example 2 by gas chromatography gives the following values:

| | |
|---|---|
| Free fatty acid | 1.07% |
| Refractive index ($n_D$ 50° C.) | 1.4649 |
| Peroxide number | 5.4 |
| Distribution of the most important fatty acids in %: | |
| C 16 | 5.6 |
| C 18 | 3.9 |
| C 18:1 | 16.0 |
| C 18:2/traces of C 20 | 73.0 |
| C 20:1 | 0.2 |
| C 22 | 0.7 |
| The tocopherol content is: | |
| α-tocopherol | 770 mg/kg |
| β-tocopherol | 30 mg/kg |
| γ-tocopherol | 10 mg/kg |
| δ-tocopherol | <5 mg/kg |

Analysis of the purified oil of Cucurbita pepo L. according to Processing example 2:

| | |
|---|---|
| Free fatty acid | 0.66% |
| Refractive index ($n_D$ 50° C.) | 1.4627 |
| Peroxide number | 5.3 |
| Distribution of the most important fatty acids in %: | |
| C 16 | 10.6 |
| C 18 | 4.9 |
| C 18:1 | 29.1 |
| C 18:2 | 54.5 |
| The following saturated fatty acids: | |
| Behenic acid | $C_{22}H_{44}O_2$ |
| Arachidic acid | $C_{20}H_{40}O_2$ |
| Stearic acid | $C_{18}H_{36}O_2$ |
| Palitic acid | $C_{16}H_{32}O_2$ |
| Myristic acid | $C_{14}H_{28}O_2$ |
| Lauric acid | $C_{12}H_{24}O_2$ |
| Caproic acid | $C_6H_{12}O_2$ |
| Isocaproic acid | $C_6H_{12}O_2$ |
| Valeric acid | $C_5H_{10}O_2$ |
| Isovaleric acid | $C_5H_{10}O_2$ |
| Butyric acid | $C_4H_8O_2$ |
| Propionic acid | $C_3H_6O_2$ |
| Acetic acid | $C_2H_4O_2$ |
| and the following unsaturated fatty acids: | |
| Oleic acid | $C_{18}H_{34}O_2$ |
| Linoleic acid | $C_{18}H_{32}O_2$ |
| Linolenic acid | $C_{18}H_{30}O_2$ |
| can be detected in the gas chromatogram. | |

The preparative separation/purification is carried out using 20×100 cm TLC plates provided with a Merck 60PF 254 silica gel layer, resp. on 20×20 cm RP-18F254 precoated TLC plates, 0.25 mm

| | |
|---|---|
| Dilution: | 1:1 with TBME/resp. CHCl$_3$ |
| Mobile phase: | chloroform/methanol/water/100% ace- |

| | |
|---|---|
| | tic acid 90/10/1/0.5 |
| Eluent: | CH$_2$Cl$_2$:ethanol 70/30 |
| R$_f$ values: | 0.30 to 0.33 |
| Application to the nano precoated TLC plate in a 10% solution with isopropyl myristate | |

The ensuing purification step is carried out using a C-18 HPLC column; dilution 1:1 THF; gradient formation.
Eluents: a) H$_2$O+0.1% TFA
b) ACN+0.1% TFA Spectral analysis demonstrates the occurrence of free sterols and/or their fatty acid esters and/or glucosides in this lipophilic constituents, of the formulae:

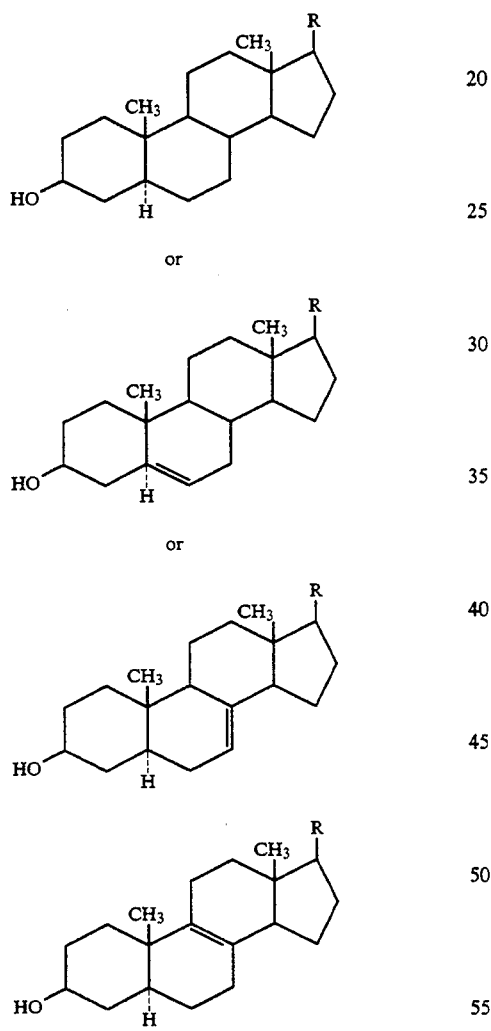

where R represents a C$_1$-C$_{10}$-alkyl or a C$_2$-C$_{10}$-alkenyl group. The alkyl or alkenyl groups in R can be straight-chain or branched and preferably have 8-10 carbon atoms in the chain. Examples of such groups are, inter alia:

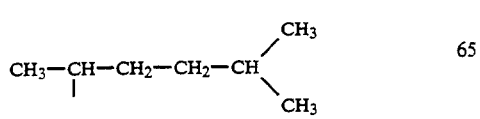

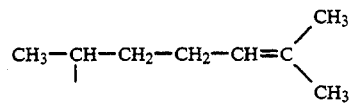

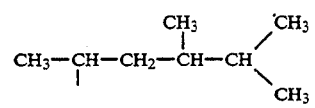

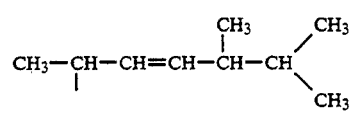

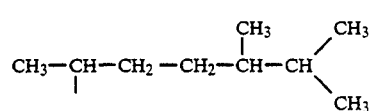

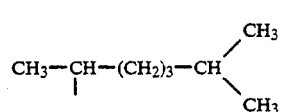

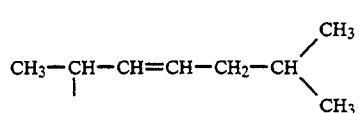

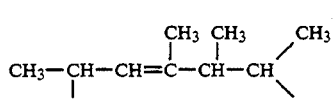

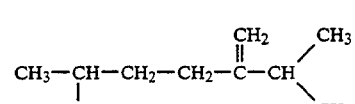

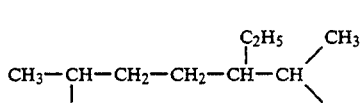

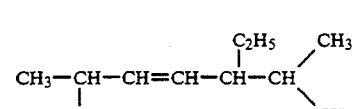

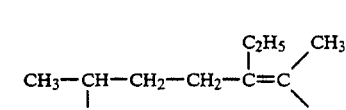

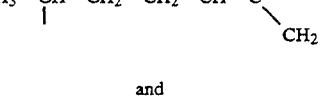

and

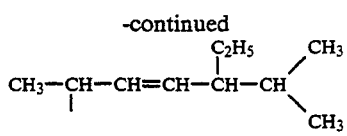

Amongst these, the most important phytosterols are:

24 β-ethylcholesta - 5,22,25 - trien - 3β-ol (25,27-dehydroporiferasterol)

24 β-ethylcholesta - 5,25 (27) - dien - 3β-ol (clerosterol)

z-ethylidencholest - 5 - en - 3β-ol (isofucosterol)

24 α-ethylcholesta - 5,22 - dien -3β-ol ($\Delta^5$-stigmasterol)

24 α-ethylcholest - 5 - en - 3β-ol ($\Delta^5$-sitosterol)

24 α-methylcholest - 5 - en - 3β-ol (campesterol)

24 β-methylcholest - 5,25 (27) - dien - 3β-ol (codisterol)

24 α-ethylidencholest 5 - en - 3β-ol ($\Delta^5$-avenasterol)

24 α-ethyl- 5α- cholesta - 7,22 - dien - 3β-ol (spinasterol)

24 α-ethyl - 5α- cholesta - 7 - en - 3β-ol (22-dihydrospinasterol)

24 α-ethylidencholest - 7 - en - 3β-ol ($\Delta^7$-avenasterol)

24 β-methyl - 5α- cholesta 7,25 (27) dien - 3β-ol (25,27-dehydrofungisterol)

24 α-ethyl - 5α- cholesta - 7,22 - dien - 3β-ol ($\Delta^7$-stigmasterol)

24 α-ethylcholest - 7 - en - 3β-ol ($\Delta^7$-sitosterol)

24 α-ethyl - 5α- cholesta - 8,22 - dien - 3β-ol and

24 β-ethyl - 5α- cholesta - 8,25(27)-dien-3β-ol

3. Processing example for the aqueous middle phase according to Processing Example 1

The material to be filtered, 16 l of the aqueous, middle phase according to Processing Example 1, is first subjected to ultrafiltration on a 0.2 μm Pellicon filter cassette (Millipore Zurich) No. GVLP 00005, filter area 0.47 m². The filtration rate is 5 l/h at 3.5 bar. The pasty retentate (0.8 l), which contains the remaining cell debris, is discarded. The filtrate (15 l) is again subjected to ultrafiltration by means of a Pellicon filter cassette with an exclusion level of 30'000 Dalton [δ] (Millipore No. PTTK 00005, filter area 0.47 m²). The filtration rate is 3 l/h at 2.5 bar. The filtrate (0.85 l) is freeze-dried. This gives a brownish powdery substance with a weight of 127 g.

As the main constituent, this substance contains 38.1% of a protein with a molecular weight of about 19'100 δ and a content of the following amino acids:

Amino acid content of the protein of about 19'100 δ:

|  | n mol | Net molecular weight | Product δ |
|---|---|---|---|
| Asp. | 14,8 | 115 | 1'702 |
| Thr. | 7,7 | 101 | 778 |
| Ser. | 11,5 | 87 | 1'001 |
| Glu. | 24,4 | 103 | 2'513 |
| Gly. | 27,8 | 57 | 1'585 |
| Ala. | 10,8 | 71 | 767 |
| Cys. | 4,8 | 103 | 494 |
| Val. | 10,3 | 99 | 1'020 |
| Met. | 5,5 | 131 | 721 |
| iso-Leu. | 8,3 | 113 | 938 |
| Leu. | 12,5 | 113 | 1'413 |
| Tyr. | 2,9 | 163 | 473 |
| Phe. | 4,8 | 147 | 706 |
| His. | 3,4 | 137 | 466 |
| Lys. | 8,6 | 128 | 1,101 |
| Arg. | 14,9 | 156 | 2'324 |
| Pro. | 10,9 | 97 | 1'057 |
|  |  |  | Σ 19'059 |

After lyophilisation, the aqueous phase of the extract of Cucurbita pepo L. seeds gives a pale brown substance which contains 17.5% of a protein of 8'734 δ and 41.4% of a protein of 20'702 δ.

The protein of 8'734 δ has the following amino acid content:

|  | n mol | Net molecular weight | Product δ |
|---|---|---|---|
| Asp. | 6,6 | 115 | 759 |
| Thr. | 2,2 | 101 | 222 |
| Ser. | 5,7 | 87 | 496 |
| Glu. | 15,3 | 103 | 1'576 |
| Gly. | 21,3 | 57 | 1'214 |
| Ala. | 6,1 | 71 | 433 |
| Cys. | 1,8 | 103 | 185 |
| Val. | 4,0 | 99 | 396 |
| Met. | 2,3 | 131 | 301 |
| iso Leu. | 3,1 | 113 | 350 |
| Leu. | 6,2 | 113 | 701 |
| Tyr. | 2,0 | 163 | 326 |
| Phe. | 2,6 | 147 | 382 |
| His. | 1,9 | 137 | 260 |
| Lys. | 5,1 | 128 | 653 |
| Arg. | 0,9 | 156 | 140 |
| Pro. | 3,5 | 97 | 340 |
|  |  |  | Σ 8'734 |

The amino acid content of the protein of 20'702 δ is:

|  | n mol | Net molecular weight | Product δ |
|---|---|---|---|
| Asp. | 21,3 | 115 | 2'450 |
| Thr. | 8,2 | 101 | 828 |
| Ser. | 13,0 | 87 | 1'131 |
| Glu. | 0,8 | 103 | 82 |
| Gly. | 17,0 | 57 | 969 |
| Ala. | 16,6 | 71 | 1'179 |
| Cys. | 0,9 | 103 | 93 |
| Val | 13,2 | 99 | 1'307 |
| Met. | 5,1 | 131 | 668 |
| iso-Leu. | 9,3 | 113 | 1'051 |
| Leu. | 17,8 | 113 | 2'011 |
| Tyr. | 6,8 | 163 | 1'108 |
| Phe. | 11,6 | 147 | 1'705 |
| His. | 5,0 | 137 | 685 |
| Lys. | 7,4 | 128 | 947 |
| Arg. | 22,3 | 156 | 3'479 |
| Pro. | 10,4 | 97 | 1'009 |
|  |  |  | Σ 20'702 |

Following ultrafiltration on the 0.2 μm Pellicon filter cassette, some of the filtrate is concentrated in vacuo and then lyophilized. Slab-gel electrophoresis demonstrates that this lyophilisate contains other proteins, of 94'000 δ, 67'000 δ and 30'000 δ.

In a comparable manner, the amino acid content was determined for two main proteins which had been obtained from the aqueous extract of Cucurbita maxima seeds according to Processing Example 1 and which have molecular weights of 19'051 δ and 30'451 δ, respectively.

4. Examples of compositions of spontaneously dispersible agents according to the invention a) 10% by weight of the lipophilic phase prepared and purified according to Processing Example 1
30% by weight of the lyophilized extract prepared according to Processing Example 3
20% by weight of ispropyl myristate
10% by weight of emulsifier mixture Diphasol ® 3873
10% by weight of Invadin ® JFC 800%
20% by weight of mannitol Diphasol ® 3873 is an emulsifier mixture consisting of 50% each of the two compounds of the formula

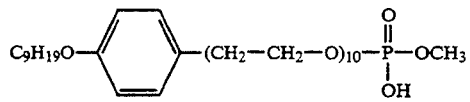

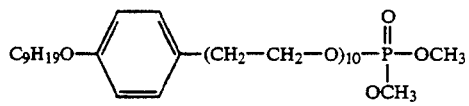

Invadin ® JFC 800% (CIBA-GEIGY) is a tert.-octylphenyl polyoxyethylene ether having 9–10 oxyethylene groups.

b) 1–5% by weight of one or more of the free sterols and/or their fatty acid esters or glucosides, separated and purified from the lipophilic phase by chromatography (cf. Processing Examples 1 and 2)
1–5% by weight free fatty acids
5–20% by weight isopropyl myristate (=isopropyl ester of myristic acid)
30–45% by weight Invadin ® JFC 800%
30–45% by weight Diphasol ® 3873 (a phosphoric acid ester surfactant)

5. Processing example: preparation of biopharmaceutical medicaments in the form of capsules, tablets, suppositories or ampuls The above-described spontaneously dispersible concentrates are processed to therapeutic systems using the following basic formulations:

|  | EURISOL ® 500 mg capsules 20 G units | | EURIKIN ® 250 mg capsules 17,5 G units | |
|---|---|---|---|---|
|  | per dose mg | batch g | per dose mg | batch g |
| Pure extract from Helianthus annuus | 15 | 3 | | |
| Pure extract from Cucurbita maxima | | | 15 | 6 |
| Oil part Hel.an. | 225 | 45 | | |
| Cuc.max. | | | 105 | 42 |

| -continued | | | | |
|---|---|---|---|---|
| β-carotene | 10 | 2 | 5 | 2 |
| α-tocopherol | 5 | 1 | 2,5 | 1 |
| Corn oil maydis germinis oleum | 200 | 40 | 100 | 40 |
| Isopropyl myristate isopropyl ester of myristic acid (Fluka) | 10 | 2 | 5 | 2 |
| Silica gel 60 ultra-pure | 25 | 5 | 12,5 | 5 |
| Invadin ® JFC 800% | 5 | 1 | 2,5 | 1 |
| Emulsifier mixture Diphasol ® 3873 | 5 | 1 | 2,5 | 1 |
| Σ | 500 | 100 | 250 | 100 |

| Guideline for use in the form of an effervescent tablet: | | |
|---|---|---|
|  | EURISOL ® EFFERVESCENT TABLETS per dose mg | EURIKIN ® per dose mg |
| Pure extract Hel.ann. | 9 | |
| Cuc.max | | 9 |
| Oil part Hel.ann. | 20 | |
| Cuc.max. | | 20 |
| β-caroe 200 ppm | 1 | 1 |
| Protein constituent | | |
| Hel.ann. | 30 | |
| Cuc.max. | | 30 |
| Eulsifiers | 10 | 10 |
| Hemp cellulose | 355 | 355 |
| NaHCO₃ | 975 | 975 |
| Citric acid crystals | 1000 | 1000 |
| Flavorings, if appr. | — | — |
| Σ | 2400 mg | 2400 mg |

N.B.: EURISOL ® und EURIKIN ® are registered trade marks of MAIGE S.A., RIEHEN

Biological assays

The antitumour action of the active substances and of the spontaneously emulsifiable concentrates, according to the Processing Examples Nos. 1–4, is confirmed by the following test results:

1. In-vitro assays using suitable tumour cell lines

A biological assay system using microtiter plates and serial dilutions has been developed. Batches of 10⁴ tumour cells per ml were set up in culture medium RPMI 1640 and inactivated with 10% of fetal calf serum (GIBCO); they are spread at a density low enough to enable them to grow during the assay, in so-called non-confluent monolayers Samples are added after 6–24 hours, with 100 μl per row, to which 100 μl of medium are added in the first well. Half of this mixture is withdrawn, transferred into the next well and again treated with 100 μl of medium, etc. This results in an n½ geometrical serial dilution.

In the plaque assay, the samples are incubated at 37° C. for 3–5 days under 3½% of CO₂. They are then stained and fixed using 0.1% crystal violet (Fluka, Buchs) in a solution of 70% of methanol, 1% of formaldehyde and 29% of water. The samples are evaluated under the microscope, magnification 300×. The greatest cytotoxic dilution is determined. The samples can also be evaluated quantitatively by means of scanning and absorption measurement in a spectrophotometer.

| EVALUATION OF THE RESULTS | | | | |
|---|---|---|---|---|
|  | TSA | BNY | 2002 | NMC |
| Tumor line Preparation | | Active in dilution to 1: | | |
| *Helianthus annuus* | | | | |
| Pure extract 1:10 | 327'600 | | | |

-continued

| EVALUATION OF THE RESULTS | | | | |
|---|---|---|---|---|
| Tumor line Preparation | TSA | BNY | 2002 | NMC |
| | | Active in dilution to 1: | | |
| 1:100 | | 163'840 ≧12'800 | | |
| | | | 6'400 | ≧12'800 |
| Oil part 1:10 | >4096 | 40'960 | | 5'120 |
| concentrate 1:10 | ≧1'280 | ≧1'280 | | |
| | | >>2'560 | | |
| *Cucurbita maxima* | | | | |
| Oil part 1:10 | | | | ≧1'280 |
| concentrate 1:10 | >1'280 | | | |
| | | >>2'560 | | |

TSA: murine adenocarcinoma (spontaneous cancer of the breast). Prof. Guido Forni, Istituto di Microbiologia, Università di Torino, Scuola di Medicina
BNY: human melanoma (Biotechnology Department, CIBA-GEIGY, Basle)
2002: FLOW human line (embryo pulmonary fibroblast)
NMC: human neuroblastoma

2. In-vivo assays on mice

The in-vivo assays were carried out on female mice. Old Balb-c strain animals of 28–32 g body weight were used (Charles River, Milan). Used as comparison standard throughout was the spontaneous adenocarcinoma TSA, a murine tumour cell line which was provided regularly by Prof. Guido Forni, Istituto di Microbiologia, Università degli Studi di Torino, Scuola di Medicina.

Feeding experiment

Carried out by Prof. Giorgio Rivara, Coordinatore sanitario USL ed Ospedale Maggiore San Giovanni Battista, LE MOLINETTE, Torino. Administration of pellets prepared from pregerminated, lyophilized homogenate from the seeds, or seed kernels, of Helianthus annuus on the one hand and Cucurbita maxima/pepo on the other hand and employed daily as the only feed, proved very palatable and acceptable. No deficiency symptoms or visible side-effects were noticed over a period of 60 days. The homogenates in this form can be classified as non-toxic.

Gavage

A series of groups of 5 test animals each were fed with ordinary test feed (NAFAG complete feed No. 850, from Nähr- und Futtermittel AG, Gossau)

The control group is given a single inguinal injection (into the left flank) of 80–100'000 cell units of the TSA tumour line, which takes very readily, shows regular subcutaneous growth and forms a solid tumour mass. 14 days after the introduction (average latency period), the newly-formed tissue is palpitated; ditto after 21 and 28, and in some cases 35, days. The mean of the length and width of the solid, distinct tumour mass under the skin is determined (post-mortem recheck).

To test the activity of the preparations in live organisms, the remaining test animals receive a daily dose of 0.2 ml of a test preparation by tube, in addition to the ordinary test feed. After an adaptation period of 3–4 days, the tumour is introduced, likewise inguinally, with 80–100'000 TSA units, as for the controls. It takes in every single case, in the group and on repetition—and provides highly comparable results, thus permitting the statistical groups to be kept to a relatively low number.

Subcutaneous injection

The experimental set-up is the same as in the case of the gavage. Instead of using a tube, the preparations to be tested are administered inguinally by injection (right flank, subcutaneously), at a rate of 0.2 ml three times per week.

| EVALUATION OF THE RESULTS | | | | | |
|---|---|---|---|---|---|
| Preparation | | TUMOR MASS Σ½ mm | | | |
| TSA | after | 14 | 21 | 28 | 35 days |
| control group | | 6 | 8 | 13 | 17 |
| *Cucurbita max.* | | 0 | 0 | 0 | 0 |
| Whole concentrate | | | | | |
| Pellets orally | | | | | |
| *Helianthus an.* | | 0 | 0 | 0 | 0 |
| Whole concentrate | | LN | LN | 0 | 0 |
| Pellets orally | | 0 | + | 2 | 2 |
| | | 0 | ++ | 3 | 5 |
| *Helianthus an.* | | 0 | 0 | 0 | 0 |
| Sp.d. concentrate | | 0 | 0 | 0 | 2 |
| 3 × 0,2 ml/week | | 0 | ++ | 3 | 6 |
| subcutaneously | | 2 | 4 | 6 | 8 |
| *Helianthus an.* | | 0 | 0 | 0 | 0 |
| fats + NAFAG | | 0 | 0 | 0 | 0 |
| orally | | 1 | 2 | 6 | 6 |
| | | 2 | 4 | 6 | 8 |
| *Helianthus an.* | | 0 | 0 | | |
| Sp.d. concentrate | | 0 | 0 | | |
| 3 × 0,2 ml/d | | 2 | 4 | | |
| orally | | 2 | 5 | | |

L.N. = lymph nodes
+ und
++ swelling

Process examples of the semisynthetic preparation of fatty acid esters of sterols, to be used according to the invention 1) 1.5 g of thionyl chloride (MW 118.77; excess) and 10 drops of dimethylformamide are added to 1 g of trans-2-dodecenic acid (MW 198.31) in 50 ml of toluene. After 20 hours at 4° C., 1 g of β-sitosterol (MW 414.72) is added to the reaction mixture. And the mixture is again left for 20 hours at 22° C., the solvent is then distilled off in vacuo and the oily residue is chromatographed on a silica gel column; eluent hexane/ethyl acetate 9:1. From the first fraction, β-sitosterol-dodecenoate (the C 12:1-sitosterol) is obtained as a yellow oil with a refractive index $n_D°$ C.=1.5118.

The following compounds are also prepared in an analogous manner:

| CHOLESTERYL-DODECENOATE | (C 12:1-CHOLESTEROL) |
|---|---|
| CHOLESTERYL-LINOLEATE | (C 18:2-CHOLESTEROL) |
| CHOLESTERYL-LINOLENATE | (C 18:3-CHOLESTEROL) |
| β-SITOSTEROL-LINOLEATE | (C 18:2-SITOSTEROL) |
| β-SITOSTEROL-LINOLENATE | (C 18:3-SITOSTEROL) |
| STIGMASTEROL-DODECENOATE | (C 12:1-STIGMASTEROL) |
| STIGMASTEROL-LINOLEATE | (C 18:2-STIGMASTEROL) |
| STIGMASTEROL-LINOLENATE | (C 18:3-STIGMASTEROL) |

2) 3 g of undecenoyl chloride and 2 g of β-sitosterol are refluxed for two hours at 80° C. in 150 ml of tetrahydrOouran. After 2 ml of pyridine or dimethylformamide have been added, the reaction is refluxed at 80° C. for another hour. The solvent is distilled off on a Rotavapor and the residue is recrystallized in acetonitrile. This gives the β-SITOSTEROLUNDECENOATE (C 11:1-SITOSTEROL), which has a melting point of 68.3° C.

The following fatty acid esters are also prepared in an analogous manner:

|  |  | m.p. °C. |
|---|---|---|
| CHOLESTERYL-CAPRYLATE | (C 8:0-CHOLESTEROL) | 106.6 |
| CHOLESTERYL-UNDECENOATE | (C 11:1-CHOLESTEROL) | 78.9 |
| CHOLESTERYL-LAUROYLATE | (C 12:0-CHOLESTEROL) | 79.4 |
| CHOLESTERYL-PALMITATE | (C 16:0-CHOLESTEROL) | 77–79 |
| CHOLESTERYL-OLEATE | (C 18:1-CHOLESTEROL) | 46 |
| β-SITOSTEROL-CAPRYLATE | (C 8:0-SITOSTEROL) | 71.3 |
| β-SITOSTEROL-LAUROYLATE | (C 12:0-SITOSTEROL) | 83.3 |
| β-SITOSTEROL-PALMITATE | (C 16:0-SITOSTEROL) | 89.6 |
| β-SITOSTEROL-OLEATE | (C 18:1-SITOSTEROL) | 52 |
| STIGMASTEROL-CARYLATE | (C 8:0-STIGMASTEROL) | 89.9 |
| STIGMASTEROL-UNDECENOATE | (C 11:1-STIGMASTEROL) | 85.7 |
| STIGMASTEROL-LAUROYLATE | (C 12:0-STIGMASTEROL) | 97.1 |
| STIGMASTEROL-PALMITATE | (C 16:0 STIGMASTEROL) | 91 |

3) To 2 g of dodecenylic acid in 200 ml of chloroform there are added 1.8 g of 1,1'carbonyl-diimidazole. The reaction solution is heated to 30° C. for 12 hours, and 4.127 g of stigmasterol are the added. After a further 12 hours at 30° C., the solvent is distilled off, and the residue is taken up in 150 ml of ethyl acetate. This solution is extracted by shaking once using 1/10N hydrochloric acid and once using 1/10N sodium hydroxide solution. After the ethyl acetate has been distilled off, the residue is taken up in a little hexane/ethyl acetate (9:1). This solution is subsequently chromatrographed on a silica gel column using hexane/ethyl acetate (9:1). The pure STIGMASTEROL-DODECENOATE (C 12:1-STIGMASTEROL), which has a refractive index of $n_D 20°$ C. = 1.4913, is obtained.

The following compounds are also prepared in an analogous manner:

| β-SITOSTEROL-DODECENOATE | (C 12:1-SITOSTEROL) |
|---|---|
| CHOLESTERYL-DODECENOATE | (C 12:1-CHOLESTEROL) |
| β-SITOSTEROL-OLEATE | (C 18:1-SITOSTEROL) |
| STIGMASTEROL-OLEATE | (C 18:1-STIGMASTEROL) |

In addition, cf. the measurement data given in the technical appendix: 1/6 to 4/6.

Process example of the semisynthetic preparation of glucosides of sterols, to be used according to the invention:

STIGMASTEROL-β-d-GLUCOSIDE

Into a 100 ml three-necked flask equipped with a distillation head, dropping funnel and magnetic stirrer there are introduced 0.5 g of stigmasterol, 0.6 g of silver carbonate and 20 ml of benzene. A solution of 1.35 g of acetobromoglucose in 30 ml of benzene is applied to the dropping funnel.

The benzene solution in the flask is heated in an oil bath until the benzene distills slightly. The benzene solution from the dropping funnel is now added dropwise with stirring in the course of about 45 minutes. The reaction mixture is stirred for another 60 minutes just below boiling point, cooled slightly and filtered, and the filtrate is evaporated to dryness in vacuo. The residue is dissolved in 20 ml of hot alcohol, 5 ml of water added, and the mixture is left overnight at 0°-5° C.

The crystals which have precipitated are filtered off and dissolved in 20 ml of warm methanol, the solution is adjusted to a pH of about 12.5 using a 5% strength solution of sodium methylate in methanol at room temperature and allowed to stand at this pH for 30 minutes. The mixture is subsequently adjusted to a pH of about 7, using acetic acid, and the mixture is evaporated to dryness.

The residue is taken up in 20 ml of chloroform/methanol 1:1, 1 g of silica gel is added, and the batch is again evaporated to dryness in vacuo.

The residue is suspended in 30 ml of chloroform/methanol 99:1, saturated with water. The suspension is suspended in a chromatography column of 20 g of silica gel in the same solvent system. The column is eluted with 100 ml portions of the same system and of chloroform/methanol 9:1 and 8:1 (always water-saturated). The product appears together with chloroform/methanol 8:2 (water-saturated). The solution is evaporated to dryness in vacuo, the product is suspended in 10 ml of hot alcohol, 3 ml of water are added to the suspension, and the mixture is left to stand overnight at 0°-5° C. The product is subsequently filtered off and dried in vacuo for 8 hours at an internal temperature of 60 ° C. This gives about 30 mg of crystalline product.

$R_f$ value in the eluent chloroform/methanol/water 15:5:2 (bottom phase): 0.4

Melting point: 255.9°-256.7° C.

In the same manner, cholesterol, sitosterol, estradiol and other steroids can be processed to give glucosides. Cf. also the information given in the technical appendix 5/6 and 6/6.

Composition examples of spontaneously dispersible agents according to the invention, which contain, as active substances, fatty acid esters of sterols according to the formulae I to X a) 7.5% by weight of a fatty acid ester of sterols (formulae I to X)

7.5% by weight of isopropyl myristate (=isopropyl ester of myristic acid)

42.5% by weight of emulsifier mixture Diphasol ® 3873 (CIBA-GEIGY)

42.5% by weight of Invadin ® JFC 800% (CIBA-GEIGY)

Diphasol ® 3873 is an emulsifier mixture consisting of 50% of each of the compounds of the formula

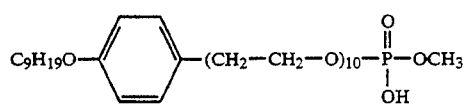

-continued

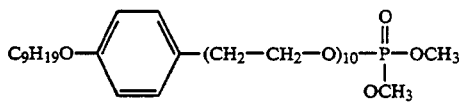

Invadin ® JFC 800% (CIBA-GEIGY) is a tert.-octylphenyl polyoxyethylene ether having 9-10 oxyethylene groups.

b) 7.5-15% by weight of one or more fatty acid esters of sterols of the formulae I to X
0-40% by weight of isopropyl myristate, olive oil or sunflower oil, cold-pressed and untreated, corn oil, wheatgerm oil or safflower oil
22.5-42.5% by weight of Diphasol ® 3873 and
22.5-42.5% by weight of Invadin ® JFC 800% c) 7.5-15% by weight of one or more fatty acid esters of sterols of the formulae I to X
0-40% by weight of isopropyl myristate
22.5-42.5% by weight of Invadin. JFC 800%
22.5-42.5% by weight of Soprophor. F1, or FLK (a phorphoric acid ester surfactant) (Rhône-Poulenc)

Processing example: preparation of biopharmaceutical medicaments in the form of micropellets, capsules, tablets, suppositories or ampuls, containing, as active substances, fatty acid esters of sterols according to formulae I to X and/or sterol-glucosides The above-described spontaneously dispersible concentrates are processed to therapeutic systems using the following basic formulations:

|  | 250 mg capsules | 500 mg capsules |
|---|---|---|
| Fatty acid esters of sterols and/or sterol-glucosides: MARIGENOL ®-CONCENTRATE (if necessary dissolved or suspended in olive oil extra vergine, resp. sunflower oil, wheatgerm oil, safflower oil or corn oil; cold pressed, untreated) | 1-25 mg | 2-50 mg |
| Distilled water (is subseq. lyophilized) | (250 mg) | (500 mg) |
| Lactose | 160-184 mg | 325-373 mg |
| Crystalline cellulose | 40 mg | 75 mg |
| Syloid 244 H | 25 mg | 50 mg |
|  | 250 mg | 500 mg |

Guideline for the preparation of so-called "multiple-unit" pharmaceuticals (micropellets or microgranules)

| CONCENTRATES | per dose | per batch |
|---|---|---|
| MARIGENOL ®-CONCENTRATE |  |  |
| with one ore more fatty acid ester sterols and/or sterol-glucosides | 20 mg | 20 g |
| Isopropyl myristate | 120 mg | 120 g |
| Invadin ® JFC 800% | 240 mg | 240 g |
| Soprophor ® FLK | 120 mg | 120 g |
| Sorbitol solution | 15 mg | 15 g |
| Sulfosalicylic acid | 15 mg | 15 g |
| Vitamin A | 10 mg | 10 g |
| α-tocopherol | 5 mg | 5 g |
| Polyethylene glycol 6000 | 10 mg | 10 g |
| Syloid ® 244 H | 10 mg | 10 g |
| (a microcrystalline cellulose) |  |  |
| MARIGENOL ®-concentrate MICROPELLETS/GRANULES | 565 mg | 565 g |
| Lactose cellulose core 80:20 |  | 495 g 28% |

| CONCENTRATES | per dose | per batch |
|---|---|---|
| MARIGENOL ®-CONCENTRATE | 565 g | 32% |
| Hydrophobic protective lacquer (for example with hydroxypropylmethyl-cellulose or EA-MMA-HEMA-Copolymer or EUDRAGIT ® E) | 70 g | 4% |
| EUDRAGIT ® L 100/L 30 D D.M. | 635 g | 36% |
|  | 1765 g |  |

Preparation carried out in a fluidized bed, or a rotating bed.
N.B. MARIGENOL ® is a registerd trade mark of MARIGEN S.A., RIEHEN.

BIOLOGICAL ASSAYS

The antitumour action of the fatty acid esters of sterols is confirmed by the following test results:

1. In-vitro assays using suitable tumour cell lines

A biological assay system using microtiter plates and serial dilutions has been developed Batches of $10^4$ tumour cells per ml were set up in culture medium RPMI 1640 and inactivated with 10% of fetal calf serum (GIBCO); the cells are spread at a density low enough to enable them to grow during the assay in so-called non-confluent monolayers. Samples are added after 6-24 hours, with 100 μl per row, to which 100 μl of medium are added in the first well. Half of this mixture is withdrawn, transferred into the next well and again treated with 100 μl of medium, etc. This results in an $n\frac{1}{2}$ geometric serial dilution.

In the plaque assay, the samples are incubated at 37° C. for 3-5 days under $3\frac{1}{2}\%$ of $CO_2$. They are then stained and fixed using 0.1% crystal violet (Fluka, Buchs) in a solution of 70% of methanol, 1% of formaldehyde and 29% water. The samples are evaluated under the microscope, magnification 300×. The greatest cytotoxic dilution is determined. The samples can also be evaluated quantitatively by means of scanning and absorption measurement in a spectrophotometer.

| EVALUATION OF RESULTS | | | | |
|---|---|---|---|---|
| MARIGENOL ® Microemulsion 0,1% containing the following fatty acid esters | Cell line TSA active in dilution to 1: | | | |
| C 11:1-CHOLESTEROL | 5 h | 1'280 | 5 d | >640'000 |
| C 11:1-SITOSTEROL | 5 h | 40 | 5 d | >640'000 |
| C 12:1-SITOSTEROL | 5 h | 640 | 5 d | 320'000 |
| C 16:0 STIGMASTEROL | 5 h | 80 | 5 d | 40'000 |
| C 18:3-SITOSTEROL | 5 h | 1'280 | 5 d | 80'000 |
| C 12:1-SITO/18:3 TSA | 5 h | 2'560 | 4 d | 40'000 |
| Human leucocytes | 1:1'000 | | | |
|  | 24 h | all cells o.k. | | |
|  | 96 h | all cells o.k. | | |
|  | 120 h | all cells o.k. | | |
| C 18:2 SITO/18:2 TSA | 5 h | 2'560 | 5 d | 20'000 |
| Human leucocytes | 1:1'000 | | | |
|  | 24 h | all cells o.k. | | |
|  | 96 h | all cells o.k. | | |
|  | 120 h | all cells o.k. | | |
| LINFOMA a cellule convolute (ST4) | | | | |
| C 12:1-SITO/18:3 0,1% microem. | | 72 h | | 1:2'500 |
| C 18:2-SITO/18:2 0,1% microem. | | 72 h | | 1:2'500 |
| LEUCEMIA a cellule T (PF 382) | | | | |
| C 12:1-SITO/18:3 0,1% microem. | | 72 h | | 1:2'500 |
| C 18:2-SITO/18:2 0,1% microem. | | 72 h | | 1:2'500 |

TSA: murine adenocarcinoma (spontaneous cancer of the breast). Prof. Guido Forni, Istituto di Microbiologia Universitá degli Studi di Torino, Scuola di Medicina

2. In-vivo assays on mice

The in-vivo assays were carried out on female mice. Old Balb-c strain animals of 28–32 g body weight were used (Charles River, Milan). Used as comparison standards throughout was the spontaneous adenocarcinoma TSA, a murine tumour cell line which was provided regularly by Prof. Guido Forni, Istituto di Microbiologia, Università degli Studi di Torino, Scuola di Medicina.

Feeding experiment

To determine the acceptability, daily doses of 0.25 ml of microemulsion of various concentrates were administered by tube over a period of 30 days. Up to 10 mg/kg of body weight, the acceptability was good.

The LD 50 is 100 mg/kg of body weight.

Gavage

A series of groups of 5 test animals each were fed with ordinary test feed (NAFAG complete feed No. 850, from Nähr- und Futtermittel AG, Gossau).

The control group is given a single inguinal injection (into the left flank) of 80–100'000 cell units of the TSA tumour line, which takes very readily, shows regular subcutaneous growth and forms a solid tumour mass. 14 days after the introduction (average latency period), the newly-formed tissue is palpitated; ditto after 21 and after 28 days, and in some cases 35, days. The mean of the length and width of the solid, distinct tumour mass under the skin is determined (postmortem recheck).

To test the activity of the preparations in live organisms, the remaining test animals receive a daily dose of 0.25 ml of a test preparation by tube, in addition to the ordinary test feed. After an adaptation period of 5–7 days, the tumour is introduced, likewise inguinally, with 80–100'000 TSA units, as for the controls. It takes in every single case, in the group and on repetition, thus permitting the statistical groups to be kept to a relatively low number.

Subcutaneous injection

The experimental set-up is the same as in the case of gavage. Instead of using a tube, the preparations to be tested are administered inguinally by injection (right flank, subcutaneously), at a rate of 0.25 ml 3 times per week.

| | | Tumor mass $\Sigma\frac{1}{2}$ L + B mm | | | |
|---|---|---|---|---|---|
| Preparation | TSA after | 14 | 21 | 28 | days |
| Control group | | 6 | 8 | 13 | |
| MARIGENOL ® | | | | | |
| 0,1% microemulsions | | | | | |
| containing | | | | | |
| β-Sitosterol-dodecenoate | | 1 | 0 | 2 | |
| Stigmasterol-dodecenoate | | 0 | 0 | 2 | |
| β-Sitosterol-linoleate | | 0 | + | 1 | |
| β-Sitosterol-linolenate | | + | + | 1 | |

+ swelling

We claim:

1. A pharmaceutical composition comprising a spontaneously dispersible concentrate which contains or a combination of antitumour components 0.001 to 15% by weight of an antitumor component selected from the group consisting of sterol fatty acid esters of the formulae:

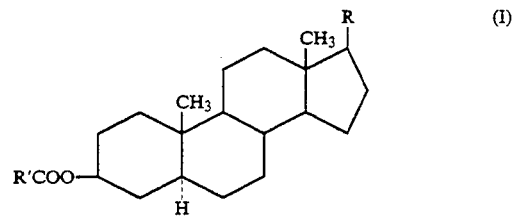

(I)

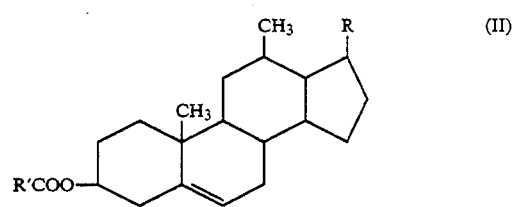

(II)

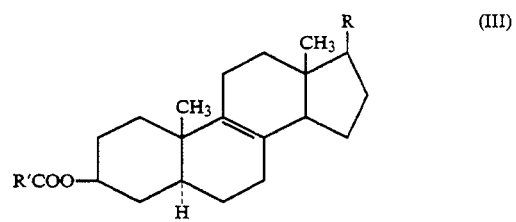

(III)

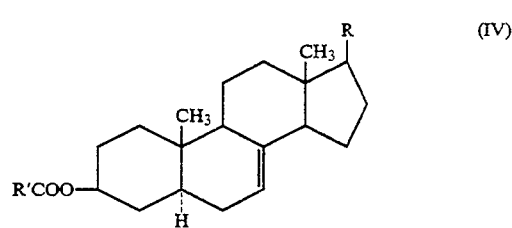

(IV)

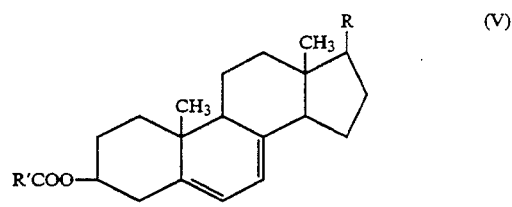

(V)

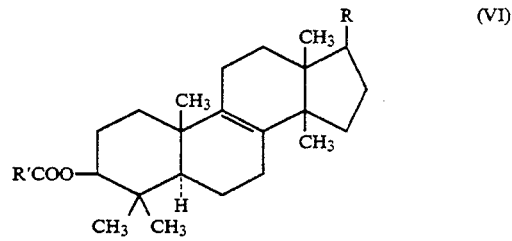

(VI)

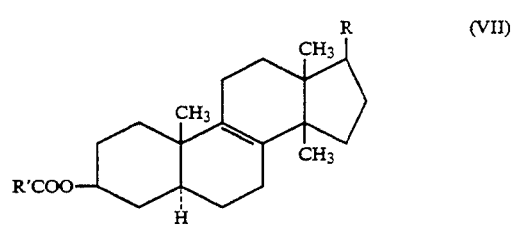

(VII)

-continued

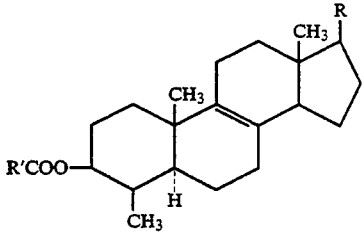 (VIII)

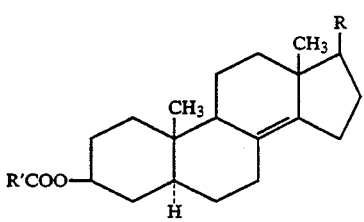 (IX)

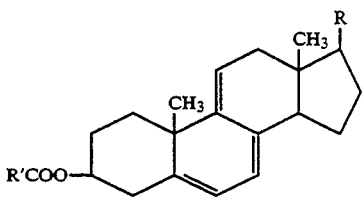 (X)

where R denotes a $C_1$- to $C_{10}$-alkyl group or a $C_2$- to $C_{10}$-alkenyl group, and R' denotes a $C_1$- to $C_{32}$-alkyl group or a $C_2$- to $C_{32}$-alkenyl group with 1 to 6 double bonds, as well as 0 to 40% by weight of a solvent or solvent mixture which is pharmaceutically acceptable and acts as a hydrotropic agent or co-emulsifier, 0.001 to 85% by weight of a pharmaceutically acceptable surfactant or surfactant mixture, 0 to 10% by weight of a vitamin or provitamin, and 0 to 10% by weight of a free fatty acid.

2. A pharmaceutical compositions comprising a spontaneously dispersible concentrate as claimed in claim 1, which contains 0.001 to 15% by weight of an antitumor component or a combination of antitumor components selected from the group consisting of sterol fatty acid esters of the formulae (I) to (X), where R denotes an alkyl or alkenyl group having 8 to 10 carbon atoms, and R' denotes an alkyl or alkenyl group having 8 to 22 carbon atoms.

3. A pharmaceutical composition comprising a spontaneously dispersible concentrate as claimed in claim 2, which contains 0.001 to 15% by weight of an antitumor component or a combination of antitumor components selected from the group consisting of STIGMASTEROL-UNDECENOATE,
STIGMASTEROL-DODECENOATE,
STIGMASTEROL-OLEATE,
STIGMASTEROL-LINOLEATE,
STIGMASTEROL-LINOLENATE, β-SITOSTEROL-UNDECENOATE,
β-SITOSTEROL-DODECENOATE,
β-SITOSTEROL-OLEATE,
β-SITOSTEROL-LINOLEATE,
β-SITOSTEROL-LINOLENATE, CHOLESTERYL-UNDECENOATE,
CHOLESTERYL-DODECENOATE,
CHOLESTERYL-OLEATE,
CHOLESTERYL-LINOLEATE, and
CHOLESTERYL-LINOLENATE.

4. A pharmaceutical composition comprising a spontaneously dispersible concentrate as claimed in claim 1, wherein the pharmaceutically acceptable surfactant or surfactant mixture (a) is selected from the group consisting of anionic, cationic, amphoteric and non-ionic surfactants; and (b) has a hydrophilic-lipophilic balance of between 2 and 18; and wherein the solvent or solvent mixture is an aliphatic ester.

5. A pharmaceutical composition as claimed in claim 4, wherein the pharmaceutically acceptable surfactant is a mixture of a non-ionic surfactant having a hydrophilic-lipophilic balance of between 2 and 6 and an anionic surfactant having a hydrophilic-lipophilic balance of between 10 and 15.

6. A pharmaceutical composition as claimed in claim 5, which contains 7.5 to 15% by weight of one or a combination of sterol fatty acid esters of the formulae (I) to (X), 22.5 to 42.5% by weight of the surfactant mixture of the following two compounds in a 1:1 ratio:

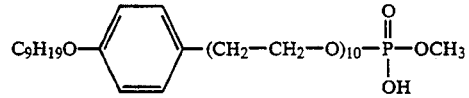

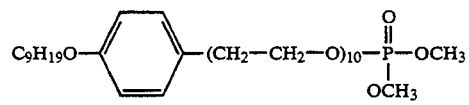

and 22.5 and 42.5% by weight of a tert.-octylphenyl-polyoxyethylether having 9 to 10 oxyethylene groups.

7. A pharmaceutical composition as claimed in claim 5, which contains 7.5 to 15% by weight of one or a combination of sterol fatty acid esters of the formulae (I) to (X), 22.5 to 42.5% by weight of a surfactant of the formula:

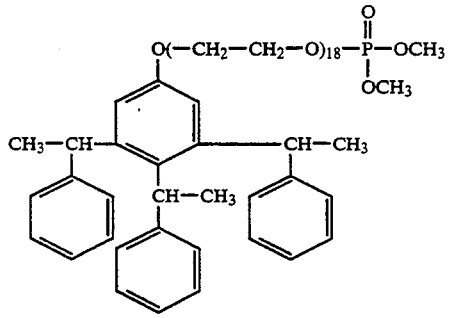

and 22.5 to 42.5% by weight of a tert.octylphenyl-polyoxyphenylether having 9 to 10 oxyethylene groups.

8. A pharmaceutical composition comprising a spontaneously dispersible concentrate according to claim 1, which further comprises an amount up to 10% by weight of a pharmaceutically acceptable excipient, diluent, stabilizer, or a combination thereof.

9. A sterol fatty acid ester selected from the group consisting of Cholesteryl-dodecenoate, β-Sitosterol-dodecenoate, and Stigmasterol-dodecenoate.

10. A process for preparing a sterol fatty acid ester selected from the group consisting of Cholesteryl-dodecenoate, β-Sitosterol-dodecenoate, and Stigmasterol-dodecenoate, which comprises (a) reacting a fatty acid of the formula:

$$CH_3-(CH_2)_4-CH=CH-(CH_2)_4-COOH$$

with carbonyldiimidazole in chloroform and in the presence of a catalytic amount of sodium methylate at a temperature between 25° and 70° C. to yield a fatty acid imidazolate, and (b) reacting said fatty acid imidazolate with Stigmasterol, β-Sitosterol or Cholesterol to yield a sterol fatty acid ester.

* * * * *

UNITED STATES PATENT AND TRADEMARK OFFICE
CERTIFICATE OF CORRECTION

PATENT NO. : 5,270,041
DATED : December 14, 1993
INVENTOR(S) : Carl Eugster, et. al.

It is certified that error appears in the above-indentified patent and that said Letters Patent is hereby corrected as shown below:

Col. 20, line 30, change "MAIGE" to --MARIGEN--.

Col. 27, line 66, insert --one-- after "contains".

Col. 1, line 37, delete "sitosterol and stigmasterol" and insert -- C 12:1-Sitosteryl-ester and C12:1-Stigmasteryl ester or Sitosteryl-docedecenoate and Stigmasteryl-dodecenoate--.

Signed and Sealed this

Ninth Day of May, 1995

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,270,041
DATED : December 14, 1993
INVENTOR(S) : Carl EUGSTER et al.

It is certified that error appears in the above-indentified patent and that said Letters Patent is hereby corrected as shown below:

In Figure 1, sheet 1 of 6, (counting text by lines), line 1, "SCHMELZPUNKTE" should read --MELTING POINTS--.

line 2, "Gemessen mit einem Mettler-Gerat TA 4000 DSC-Verfahren" should read --Measured with a Mettler Apparatus TA 4000 DSC method--.

line 4, delete "bzw. mit einem Buchi-Gerat" should read --or using a Buechi Apparatus--.

line 5, "MESSWERT" should read --DATA--;

line 5, "ENDOTHERME" should read --ENDOTHERMIC--.

UNITED STATES PATENT AND TRADEMARK OFFICE
CERTIFICATE OF CORRECTION

PATENT NO. : 5,270,041
DATED : December 14, 1993
INVENTOR(S) : Carl EUGSTER et al.

It is certified that error appears in the above-indentified patent and that said Letters Patent is hereby corrected as shown below:

line 6, "VERBINDUNG (Smp)" should read --COMPOUND m.p. °C--;

line 6, "REAKTION" should read --REACTION °C--.

line 22, "BRECHUNGSINDEX" should read --REFRACTIVE INDEX--.

line 23, "Gemessen mit einem Zeiss-Refraktometer" should read --Measured using a Zeiss Refractometer--.

line 24, "VERBINDUNG MESSWERT" should read --COMPOUND DATA--.

Figure 2, sheet 2 of 6, line 3, "Endotherme Reaktion" should read --Endothermic reaction--;

line 13, "Endotherme Reaktion" should read --Endothermic reaction--.

Figure 3, sheet 3 of 6, line 1, "Rf - WERTE" should read --Rf VALUES--.

UNITED STATES PATENT AND TRADEMARK OFFICE
CERTIFICATE OF CORRECTION

PATENT NO. : 5,270,041
DATED : December 14, 1993
INVENTOR(S) : Carl EUGSTER et al.

It is certified that error appears in the above-indentified patent and that said Letters Patent is hereby corrected as shown below:

line 2, "1%-Losung in $CH_2Cl_2$, bandformig aufgetragen 2 cm/2µl" should read --1% strength solution in $CH_2Cl_2$, applied bandwise 2 cm/2µl--.

line 4, "nach" should read --after--.

line 7, "VERBINDUNG" should read --COMPOUND--.

line 24, "Erklarung" should read --EXPLANATION--.

line 25, "Platte Merck Art. 5715 Petrolether/Diethylether" should read --Merck plate, 5715 Petroleum ether/diethyl ether--.

line 26, "do." (both occurrences) should read --ditto--.

line 27, "do. Cyclohexan/Ethylacetat" should read --ditto Cyclohexane/ethyl acetate--.

line 28, delete "Platte".

line 29, "Petrolether/Diethylether" should read --petroleum ether/diethyl ether--.

UNITED STATES PATENT AND TRADEMARK OFFICE
CERTIFICATE OF CORRECTION

PATENT NO. : 5,270,041
DATED : December 14, 1993
INVENTOR(S) : Carl EUGSTER et al.

It is certified that error appears in the above-indentified patent and that said Letters Patent is hereby corrected as shown below:

line 30, "do. n-Hexan/t.Butylmethylether/Aceton" should read --ditto n-Hexane/t.butyl methyl ether/acetone--.

lines 32 and 33, "do. Petrolether/Cyclohexan/Ethylacetat/$H_2O$" should read --ditto Petroleum ether/cyclohexane/ethyl acetate/$H_2O$--.

line 34, "do. Petrolether/Diethylether" should read --ditto Petroleum ether/diethyl ether--.

Figure 4:
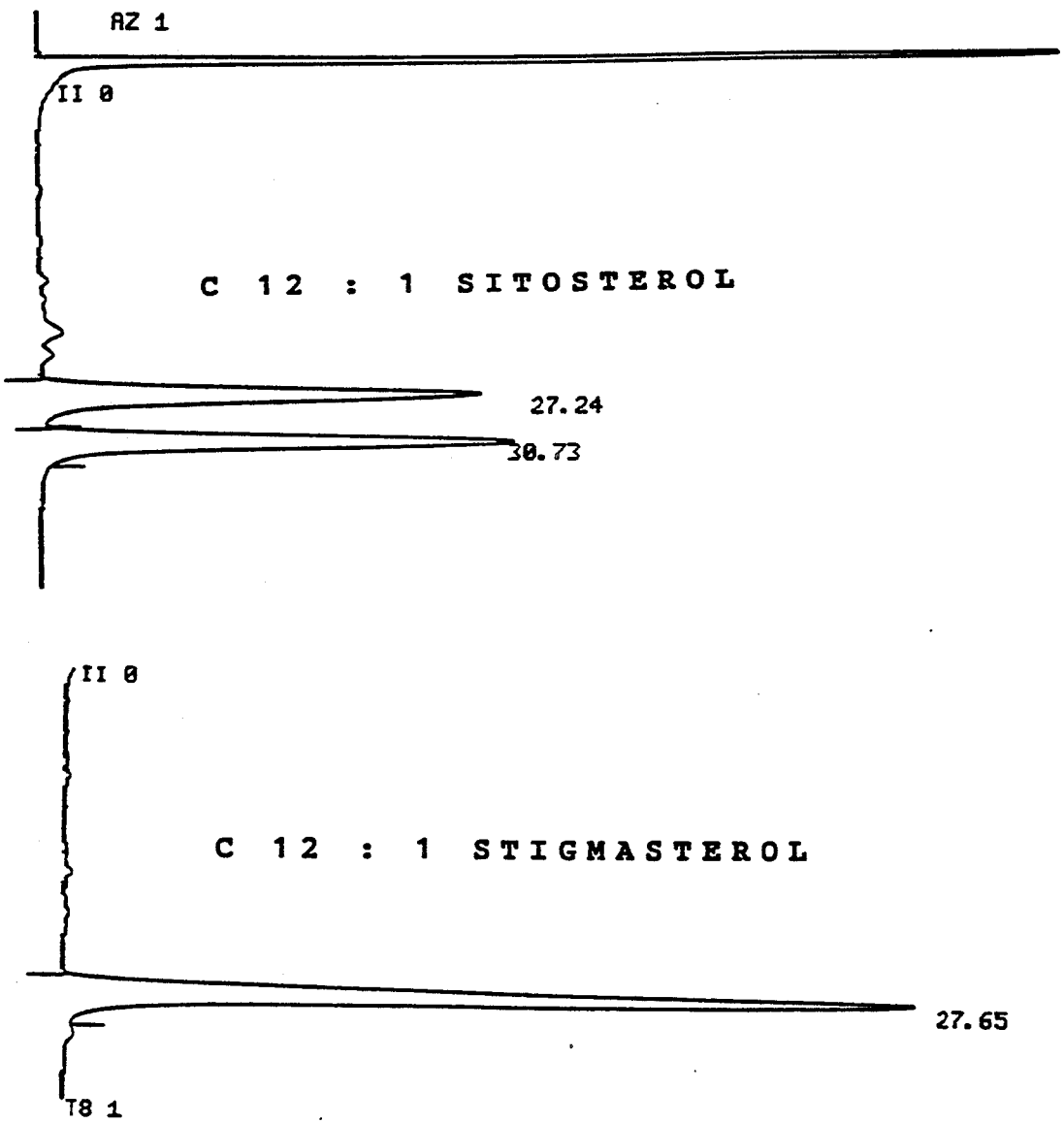
FIG. 4 shows the HPLC analyses for sitosterol and stigmasterol.

Figure 4, sheet 4 of 6, line 1, "HPLC - ANALYSE" should read --HPLC ANALYSIS--.

line 2, "Saule 25 cm/4,6 mm mit" should read --Column: 25 cm/4.6 mm, packed with--.

line 3, "Eluiermittel" should read --Eluent--.

line 4, "ca." should read --approx.--.

line 5, "Detektor U V" should read --U V detector--.

Figure 5, sheet 5 of 6, line 1, "GLUCOSID" should read --GLUCOSIDE--.

UNITED STATES PATENT AND TRADEMARK OFFICE
CERTIFICATE OF CORRECTION

PATENT NO. : 5,270,041
DATED : December 14, 1993
INVENTOR(S) : Carl EUGSTER et al.

It is certified that error appears in the above-indentified patent and that said Letters Patent is hereby corrected as shown below:

line 2, "Rf - WERTE" should read --Rf VALUES--.

line 3, "Auftrag 2 mg/1 ml = 0,2 % Losung" should read --Application: 2 mg/1 ml = 0,2 % strength solution--.

line 5, "im Wasserbad auf 60 °C anwarmen" should read --heat to 60 °C using water bath--.

line 10, "Erlauterung" should read --Explanation--.

line 13, "Essigsaure" should read --acetic acid--.

line 14, "Ameisensaure" should read --formic acid--.

Figure 6:
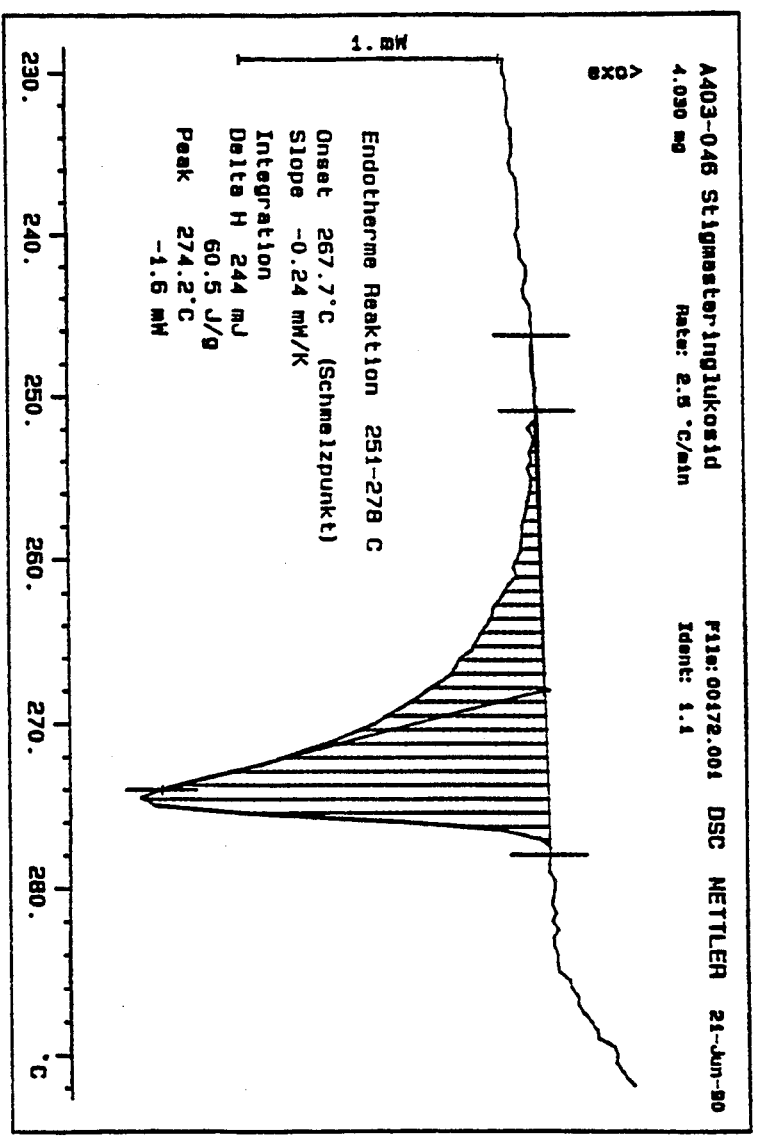
FIG. 6 is a density scanning calorimetry graph for stigmasterol-beta-d-glucoside.

Figure 6, sheet 6 of 6, line 3, "Gerat" should read --Apparatus--.

above chart "GLUCOSID" should read --GLUCOSIDE--.

inside chart, line 1, "Stigmasteringlukosid" should read --stigmasterol-glucoside--.

line 3, "Endotherme Reaktion" should read --Endothermic reaction--.

UNITED STATES PATENT AND TRADEMARK OFFICE
CERTIFICATE OF CORRECTION

PATENT NO. : 5,270,041
DATED : June 1, 1993
INVENTOR(S) : Carl EUGSTER et al.

It is certified that error appears in the above-indentified patent and that said Letters Patent is hereby corrected as shown below:

line 4, "(Schmelzpunkt)" should read --(melting point)--.

Column 1, lines 36-37, "sitosterol and stigmasterol" should read --C 12:1-Sitosteryl-ester and C12:1-Stigmasteryl ester or Sitosteryl-dodecenoate and Stigmasteryl-dodecenoate--.

lines 66-67, delete "or a combination of antitumour components";

line 68, after "component" insert --or a combination of antitumour components--.

Signed and Sealed this

Twenty-seventh Day of February, 1996

Attest:

BRUCE LEHMAN

*Attesting Officer*     *Commissioner of Patents and Trademarks*